(12) United States Patent
Siegel et al.

(10) Patent No.: US 11,636,627 B2
(45) Date of Patent: Apr. 25, 2023

(54) SYSTEM FOR HISTOLOGICAL EXAMINATION OF TISSUE SPECIMENS

(71) Applicant: AUGMENTIQS MEDICAL LTD., Misgav (IL)

(72) Inventors: Gabriel Siegel, Moreshet (IL); Dan Vadim Regelman, Kirtay Bialik (IL)

(73) Assignee: Augmentiqs Medical Ltd., Misgav (IL)

( * ) Notice: Subject to any disclaimer, the term of this patent is extended or adjusted under 35 U.S.C. 154(b) by 0 days.

(21) Appl. No.: 16/328,573

(22) PCT Filed: Jun. 25, 2017

(86) PCT No.: PCT/IL2017/050702
§ 371 (c)(1),
(2) Date: Feb. 26, 2019

(87) PCT Pub. No.: WO2018/042413
PCT Pub. Date: Mar. 8, 2018

(65) Prior Publication Data
US 2020/0211233 A1 Jul. 2, 2020

Related U.S. Application Data

(60) Provisional application No. 62/380,425, filed on Aug. 28, 2016.

(51) Int. Cl.
*G06T 11/00* (2006.01)
*G02B 21/18* (2006.01)
(Continued)

(52) U.S. Cl.
CPC .............. *G06T 11/00* (2013.01); *G02B 21/18* (2013.01); *G06F 3/013* (2013.01); *H04N 23/55* (2023.01); *H04N 23/56* (2023.01)

(58) Field of Classification Search
None
See application file for complete search history.

(56) References Cited

U.S. PATENT DOCUMENTS 4,720,804 A * 1/1988 Moore ................... G02B 21/00
33/298
5,601,549 A 2/1997 Miyagi
(Continued)

FOREIGN PATENT DOCUMENTS

CN 1373857 A 10/2002
CN 101470219 A 7/2009
(Continued)

OTHER PUBLICATIONS

Google search Report.*
(Continued)

*Primary Examiner* — Mohammad J Rahman
(74) *Attorney, Agent, or Firm* — Smith Gambrell & Russell LLP

(57) ABSTRACT

An interactive apparatus, system and method for image capturing and projecting is integrated into an optical microscope. An image capturing and projecting unit is operatively connected to a processing unit, the processing unit configured to: (a) receive user generated data; and (b) overlay the user generated data onto an optically viewed image visible through the eyepiece.

13 Claims, 17 Drawing Sheets

(51) Int. Cl.
  *G06F 3/01*       (2006.01)
  *H04N 5/225*      (2006.01)
  *H04N 23/55*      (2023.01)
  *H04N 23/56*      (2023.01)

(56) References Cited

U.S. PATENT DOCUMENTS

| | | | | |
|---|---|---|---|---|
| 5,867,308 | A * | 2/1999 | Pensel | A61B 3/0025 359/368 |
| 6,081,371 | A | 6/2000 | Shioda et al. | |
| 7,092,153 | B1 * | 8/2006 | Atchison | G02B 7/008 359/368 |
| 7,365,738 | B2 | 4/2008 | Molander et al. | |
| 8,755,579 | B2 * | 6/2014 | Soenksen | G02B 21/002 382/128 |
| 8,798,394 | B2 * | 8/2014 | Lett | G01N 21/6428 382/100 |
| 9,271,648 | B2 | 3/2016 | Durnell et al. | |
| 9,418,421 | B1 * | 8/2016 | Neishaboori | G06T 7/277 |
| 10,274,714 | B2 | 4/2019 | Hauger et al. | |
| 2001/0021063 | A1 * | 9/2001 | Knebel | G02B 21/0032 359/385 |
| 2003/0069471 | A1 | 4/2003 | Nakanishi et al. | |
| 2004/0109169 | A1 * | 6/2004 | Olschewski | G02B 21/365 356/609 |
| 2004/0159773 | A1 * | 8/2004 | Fein | G01N 21/6458 250/208.1 |
| 2006/0291712 | A1 * | 12/2006 | Popescu | G01N 33/49 382/134 |
| 2007/0066967 | A1 * | 3/2007 | Sieckmann | G01N 1/2813 606/10 |
| 2007/0097496 | A1 * | 5/2007 | Ulrich | G02B 21/08 359/385 |
| 2007/0138371 | A1 * | 6/2007 | Marshall | G01S 7/4812 250/201.3 |
| 2007/0211256 | A1 * | 9/2007 | Medower | G01B 9/0201 356/491 |
| 2007/0216906 | A1 * | 9/2007 | Javidi | G06K 9/00134 356/457 |
| 2008/0129677 | A1 * | 6/2008 | Li | G09G 3/3611 345/102 |
| 2009/0091566 | A1 * | 4/2009 | Turney | G06T 7/33 345/419 |
| 2010/0177185 | A1 * | 7/2010 | Woerlein | A61B 90/36 348/77 |
| 2010/0245557 | A1 | 9/2010 | Luley, III et al. | |
| 2012/0046536 | A1 * | 2/2012 | Cheung | A61B 34/20 600/407 |
| 2012/0183198 | A1 * | 7/2012 | Zahniser | G06T 7/0014 382/133 |
| 2012/0224044 | A1 * | 9/2012 | Lett | G01N 21/6428 348/79 |
| 2013/0010097 | A1 * | 1/2013 | Durnell | A61B 3/113 348/78 |
| 2013/0044185 | A1 * | 2/2013 | Krishnaswamy | A61B 5/0073 348/45 |
| 2014/0015954 | A1 * | 1/2014 | Tsujimoto | G02B 21/36 348/79 |
| 2014/0169655 | A1 * | 6/2014 | Van Leeuwen | G02B 21/244 382/133 |
| 2014/0192407 | A1 * | 7/2014 | Greenberg | G02B 21/086 359/385 |
| 2016/0170196 | A1 | 6/2016 | Rossmann et al. | |
| 2016/0202150 | A1 | 7/2016 | Schlaudraff | |
| 2017/0031146 | A1 * | 2/2017 | Zheng | H04N 5/23212 |
| 2017/0049322 | A1 * | 2/2017 | Heeren | A61B 3/102 |
| 2017/0242133 | A1 * | 8/2017 | Yilmaz | G01C 21/206 |
| 2017/0245954 | A1 * | 8/2017 | Beira | A61B 34/37 |
| 2018/0031817 | A1 * | 2/2018 | Barral | G16H 10/40 |
| 2018/0157020 | A1 * | 6/2018 | Kamada | G02B 21/0076 |

FOREIGN PATENT DOCUMENTS

| | | |
|---|---|---|
| CN | 102782558 A | 11/2012 |
| CN | 103091844 A | 5/2013 |
| DE | 10009532 A1 | 8/2001 |
| DE | 102004038001 A1 | 4/2005 |
| DE | 102014207130 A1 | 8/2015 |
| JP | H07333522 A | 12/1995 |
| JP | 2001112776 A | 4/2001 |
| JP | 3109041 B | 3/2012 |
| JP | 4956691 B | 3/2012 |
| JP | 2014143595 A | 8/2014 |
| JP | 2016114943 A | 6/2016 |
| WO | WO2014178228 A1 | 11/2014 |
| WO | 2016130424 | 8/2016 |
| WO | 2016130424 A1 | 8/2016 |
| WO | WO2016130424 | 8/2016 |
| WO | WO2016127088 A1 | 11/2016 |

OTHER PUBLICATIONS

IP.com search Report.*
The First Office Action released in corresponding Chinese Patent Application No. 201780052997 dated Feb. 4, 2021; 12 pages.
The Office Action released by the Japanese Patent Office dated Aug. 3, 2021 for corresponding Japanese Patent Application No. 2019-532224; 15 pages.
The Office Action released by the Indian Patent Office dated Sep. 10, 2021 for corresponding Indian Patent Application No. 201917009626; 6 pages.
The Second Office Action released by the Chinese Patent Office dated Jul. 29, 2021 for corresponding Chinese Patent Application No. 201780052997.7; 12 pages.

* cited by examiner

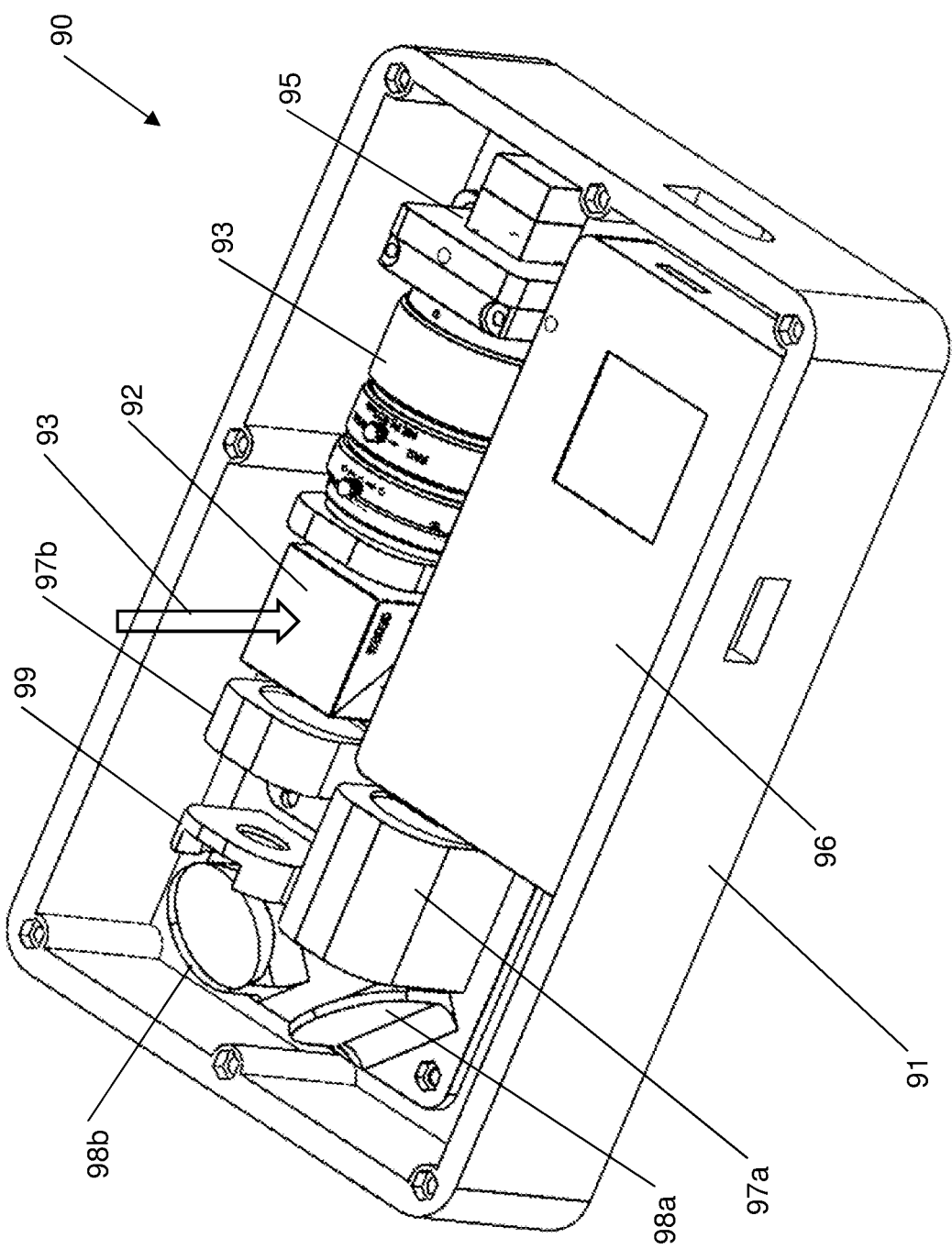
Fig. 4A(ii)

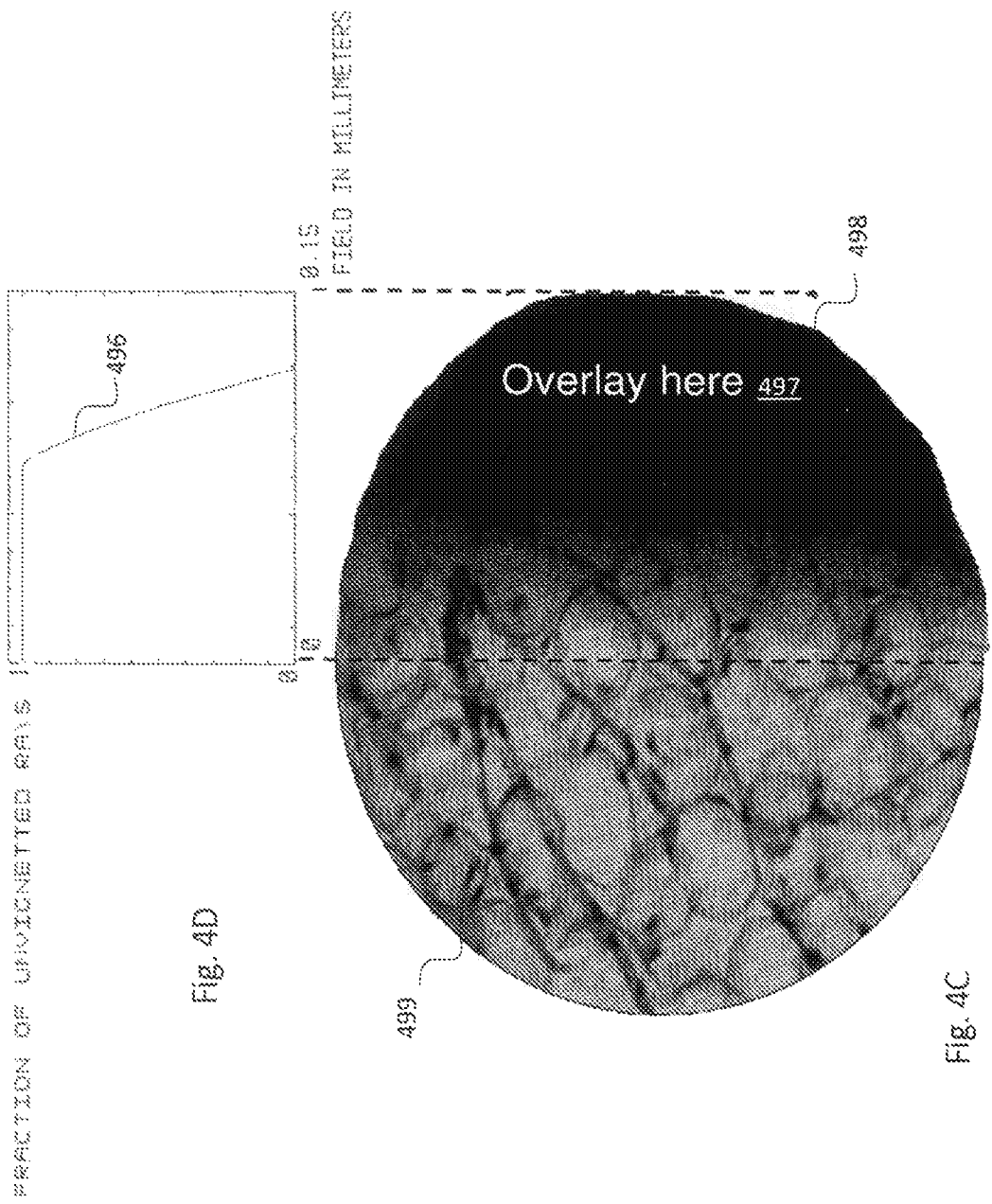

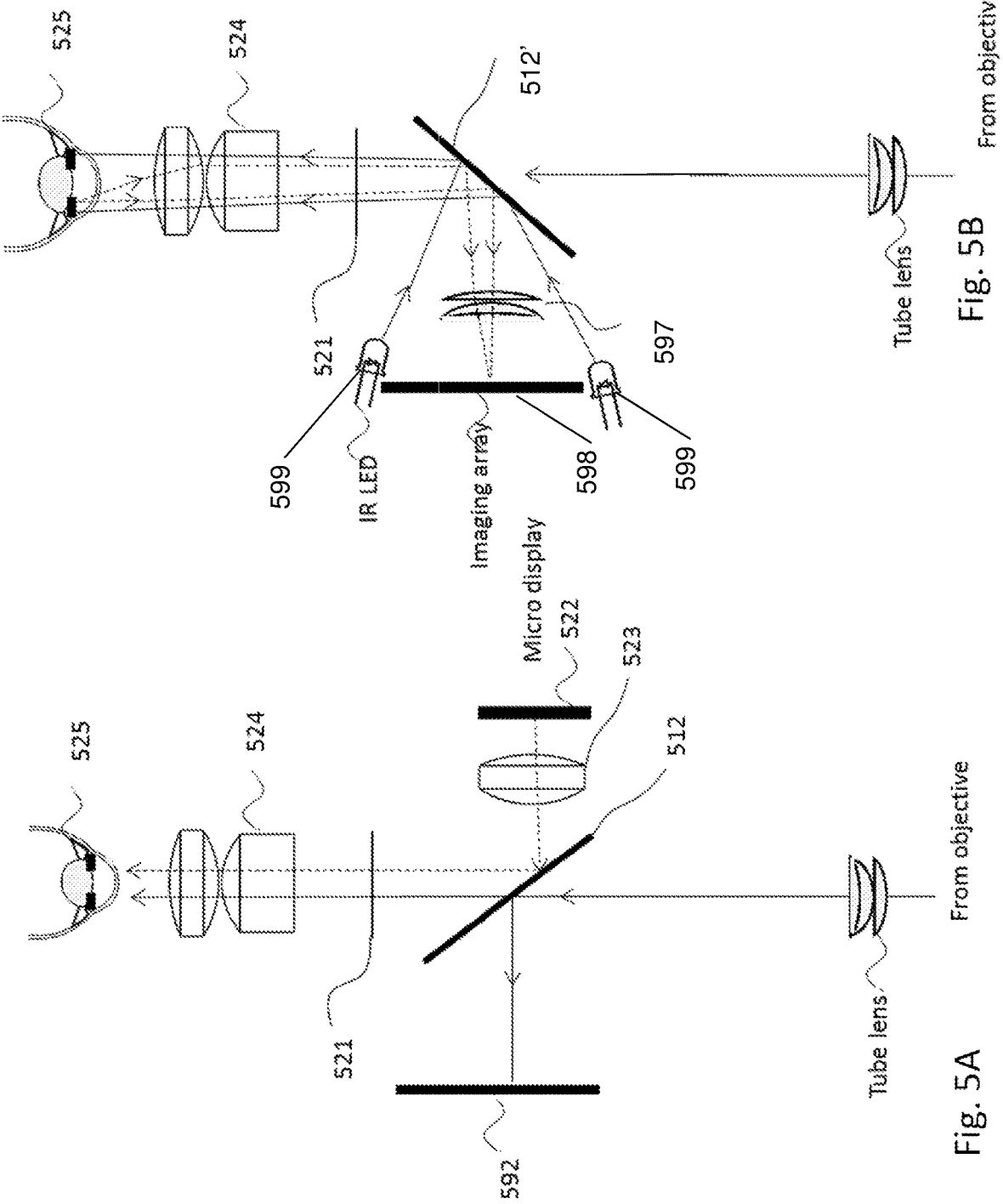

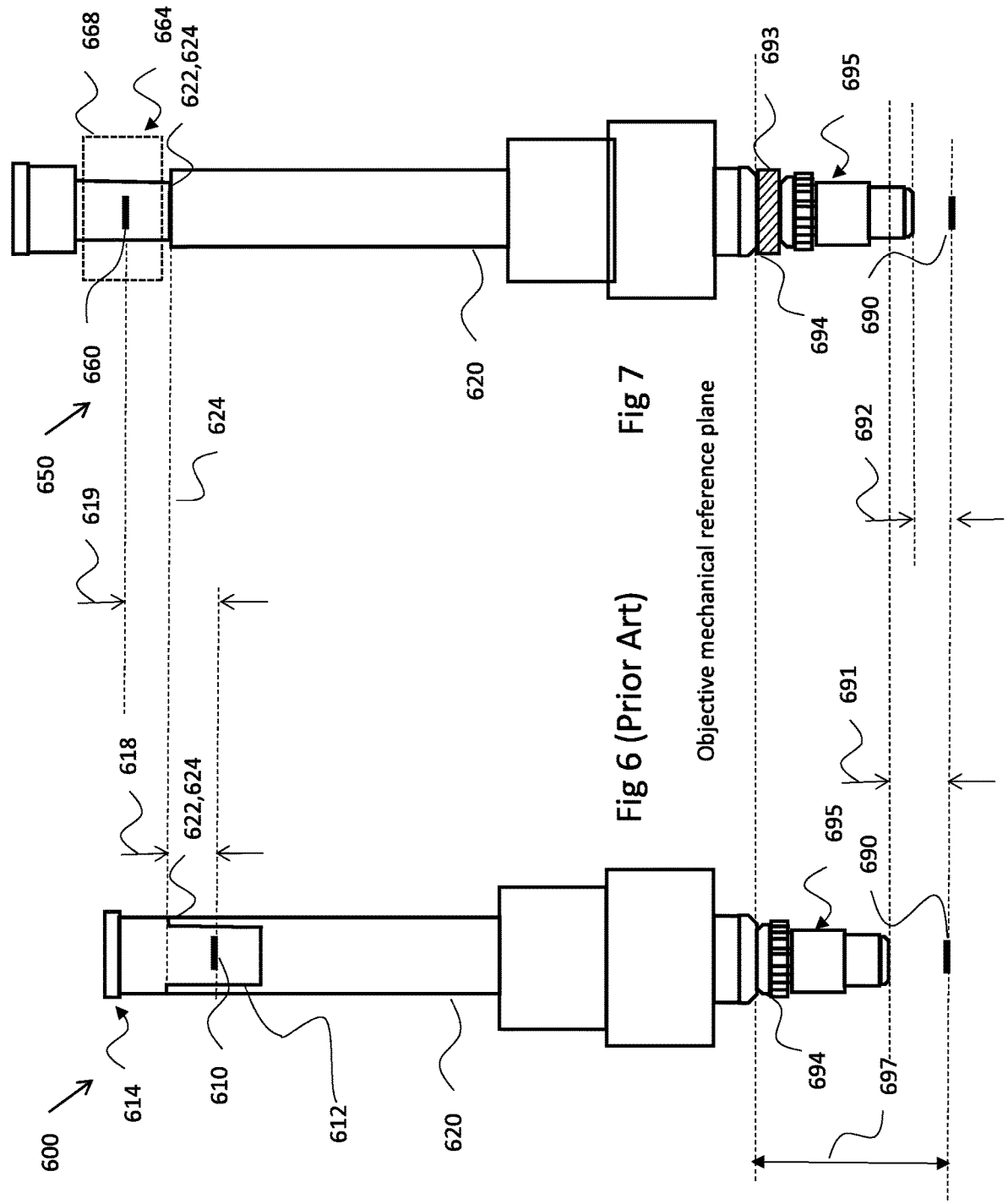

SYSTEM FOR HISTOLOGICAL EXAMINATION OF TISSUE SPECIMENS

CROSS-REFERENCE TO RELATED APPLICATIONS

The present application is a National Phase filing under 35 U.S.C. § 371 of International Patent Application No. PCT/IL2017/050702, filed Jun. 25, 2017, which is based upon and claims the benefit of the priority date of U.S. Provisional Patent Application Ser. No. 62/380,425, filed Aug. 28, 2016, each of which is expressly incorporated herein by reference in its entirety.

FIELD OF THE INVENTION

The present invention relates to the field of manual and automated microscopy, and particularly to a microscope having an eyepiece, an illumination beam path serving to illuminate a specimen, and a detection beam path that images the specimen, where additional data can be overlaid within the eyepiece, and methods for operations thereof.

BACKGROUND OF THE INVENTION

Microscopes have been in use for over 200 years, with few conceptual changes to their design and use over this period. However, for a busy microscope user, such as, but not limited to a pathologist, the operation of a microscope is not necessarily efficient in terms of reaching the best diagnosis, or completing a case report.

Currently when beginning a specimen examination, a microscope user looks through the eyepieces in order to view the specimen. The user then makes a decision or diagnosis based on characteristics or features of the specimen according to their best judgement. In other words, the user reaches a decision based primarily on the optical image in the eyepiece, and is generally not using other computer assisted tools to help reach a decision, nor other data sets such as patient data or comparable specimens.

Moreover, there is currently no effective method for auditing work performed by the user, nor is the user able to effectively consult with colleagues about the specimen. At a later point in time, there is no verifiable way to know what work was performed, what was the image used for reaching a specific conclusion, or how the diagnosis was reached.

While today, many microscopes enable imaging cameras within the third ocular that are used to capture images into a personal computer station where they can be further analyzed and saved as reports, it has been found that many microscope users do not generally use these imaging cameras due to their slowing down the workflow.

Furthermore, following diagnosis, the user must then stop using the microscope in order to create a case report. In this context, the user is forced to spend time away from the microscope to complete tasks which are not part of the core work. This is a time-consuming situation which does not lend well to improving specimen diagnosis workflow.

Specifically:

The microscope is the most important tool in clinical and toxicological pathology, where each sample is examined under the microscope lens for presence of various significant pathologies manifested by the tissue cells physical or chemical properties.

To date, two primary methods exist for microscopic examination: manual microscopy and automated whole slide imaging.

In practical clinical or pharmaceutical research settings using manual microscopy, the examined slides throughput is as important as the analysis accuracy. When required, a comparison with other slides is done manually by interchanging the slides under the microscope. Digital photography of the specimen is done only occasionally, since it requires an additional step of using a computer for data grabbing, storage, analysis and reporting.

Among the striking advantages of a manual microscopy is the utilization of human perception, allowing very fast scanning of a slide area and identification of Regions Of Interest (ROI) for a deeper examination. The abilities of a well trained professional are yet to be matched by computer algorithms, although many attempts are made into this direction. Yet another advantage is accurate non-mediated perception of colors and depth of field that is hard to reproduce by imaging sensor and a monitor.

Moreover, lack of routine photography in practical clinical settings limits generation of clinical data arranged in databases that is a critical component of development of automated diagnostics and/or diagnostics support algorithms.

Automated whole slide imaging microscopy generates a multiple resolutions/focal plane scanned images of the whole slide area by scanning the slide and storing the information into a computer system. Within the limitations of the present technology the scanning/information retrieval takes substantially longer time as compared to manual microscopy. For example, comparison of digital whole slide imaging system with manual microscopy revealed a 13 times longer timeframes for the automated systems ("Using computerized workflow simulations to assess the feasibility of whole slide imaging full adoption in a high-volume histology laboratory" McClintock, Lee, Gilbertson). This drawback imposes significant hurdles for practical deployment of those systems.

This situation exists for at least two decades.

Some background information can be found in the following US patent and patent applications which are incorporated herein by reference:

U.S. Pat. No. 9,271,648; to Durnell, et al.; titled "Eye tracking apparatus"; discloses an eye tracking apparatus for monitoring a user's eye, for use in conjunction with secondary optical apparatus such as binoculars or night vision goggles.

US application 20100245557; to Luley, III, et al.; titled "INJECTION OF SECONDARY IMAGES INTO MICROSCOPE VIEWING FIELDS"; discloses systems and methods for injecting secondary images into viewing fields of surgical microscopes. Some exemplary embodiments may provide secondary image injection in a picture-in-picture arrangement, thereby allowing a surgeon to simultaneously view the one or more secondary images and the surgical field through the oculars of the surgical microscope. Some exemplary embodiments may allow injection of secondary images including live video, such as live images from an endoscope, as well as previously obtained images, such as stored images from pre-operative studies.

US application 20160202150; to Schlaudraff Falk; titled "LASER MICRODISSECTION SYSTEM AND LASER MICRODISSECTION SYSTEM METHOD"; discloses a laser microdissection system includes a microscope that includes a reflected light device having a laser deflector which guides a laser beam provided by a laser through a microscope objective of the microscope onto a sample region for receiving a biological sample and which moves a point of impingement of the laser beam in the sample region.

U.S. Pat. No. 7,365,738, titled "Guides and indicators for eye movement monitoring systems", discloses an eye tracking apparatus monitors a user's eye orientation while the user views a video display.

The present invention allows for overcoming the above drawbacks of both manual and automated methods, keeping a fast manual workflow (based on direct optical observation via the microscope) with digital data collection and computerized tools for image analysis found in automated whole slide imaging.

SUMMARY OF THE EMBODIMENTS

According to another aspect of the presently disclosed subject matter, there is provided a system retrofitting an optical microscope by inserting an electro-optical unit into the optical accessory bay of the microscope or other suitable port within the image optical path of the microscope, such that the system enables viewing of the optical imaging plane, acquisition of digital images from the optical imaging plane, and a display of pointers and digital information as an overlay on the optical image of the specimen.

In an exemplary embodiment, the electro-optical unit is inserted at or near the Fourier plane of the optical train. The electro-optical unit comprises an image capture and image projection units.

In an exemplary embodiment, the electro-optical unit has a form-factor that allows it to be inserted into the optical train of a standard microscope, for example in the filter's bay.

In another exemplary embodiment, the standard camera port of the microscope is used for image capturing, and the image projection unit is inserted in another location along the optical train.

In yet another exemplary embodiment, the microscope is designed and manufactured with an image capturing and an image projection unit as integral parts of the microscope.

According to another aspect of the presently disclosed subject matter, there is provided a system retrofitting the eyepiece or other suitable port within the image optical path of the microscope, such that the system enables viewing of the optical imaging plane, acquisition of digital images from the optical imaging plane, and a display of pointers and digital information as an overlay on the optical image of the specimen. The overlaid information may include digital textual data, dimensional measurements, image enhancements, previously acquired images or image parts, etc., in addition to other types of user generated data.

The system comprises a micro display for generating the overlay data, a digital imaging array for capturing images from the optical image path, optical and mechanical means to combine the images from the micro-display into the optical image path, a computing module and user interface devices.

According to another aspect of the presently disclosed subject matter, there is provided an interactive eyepiece operatively connected to a data processing unit, where the data processing unit is configured to: (a) receive user generated data; and (b) overlay the user generated data onto an image visible through the microscope eyepiece.

In some cases, the eyepiece enables display of an image acquired by the device along with an overlay of user generated data.

According to yet another aspect of the presently disclosed subject matter, there is provided a method of operating an interactive microscope, where the method comprises: (a) receiving user generated data; and (b) overlaying the user generated data onto an image visible through the eyepiece.

In particular, one aspect of the present invention is a method for selective darkening of parts of the optical image for the purpose of exclusive display of the overlay image, while in other optical image areas, a combination of both optical and digital overlay images would appear.

Yet another aspect of the present invention is the method of mass, automatic selection of specimen areas where digital images are acquired, labeled and stored. Those images might further be used for training algorithms for automated detection of pathologies, big data analysis, tele-pathology, commercialization of an image database, or other purposes.

One of the critical requirements for development of automated algorithms for pathology detection and classification is the existence of a large enough training set. Generation of such a dataset is not practical within the existing time limited workflow of a user's clinical workflow. Automated whole slide imaging methods generate vast amount of data, most of which has no relevance to the algorithms training tasks. Some embodiments of the present invention allow automatic generation of such a dataset without any special effort from the user. Every time an image is acquired it is stored into the database. If geometric forms are drawn and/or measured—the area is tagged as a potential pathology. The imaging sensor constantly acquires images and processes them to determine whether the slide is moving or at rest. This could be achieved by a variety of algorithms, such as but not limited to, evaluating average image blur and contrast gradients strength. Moving slide will have low gradients contrast and high blur, while static slide will have opposite properties. Every time a slide is at rest an image is acquired and stored into the database is tagged as a potential region of interest for a detection of pathology.

By using feature tracking image processing techniques such as active contours, a relative position of the slide with respect to the original point can be determined and displayed to the user, marked on the acquired and stored images and delivered to the report. This feature would enable a user to return to the detected feature on the slide later when necessary without manual search.

Another method for determination of the potential pathology region of interest is based on tracking the observer's line of sight (user's gaze), for example based on the pupil position. In many cases the slide scanning rate is slow enough, so initial observation of a suspicious region is performed without actual stopping of the scanning, but by locking the eye line of sight (gaze) onto a particular area on the slide image. In this case a "locked" gaze onto a specific point exceeding a predefined time period, typically about 250 ms, would also trigger an image acquisition and storage into the database as a potential pathology.

Using the above methods, a database including images tagged as "pathological" (those marked with the geometric shapes and/or measurements or actively acquired by the user), "highly suspicious" (those acquired automatically when the observer stopped and resumed the scanning process) and "low level suspicious" (those acquired automatically when the observer locked his gaze onto a particular area on the slide).

Yet another aspect of the present invention is the method of keeping the correct focus of the imaging pane when integrating the abovementioned system.

It should be noted that the current invention may also be adopted to be used in an inverted microscope.

According to another aspect of the present disclosed subject matter, an apparatus for image capturing and image projecting is provided, the apparatus comprising: a digital camera for capturing digital images; a digital image projector for generating projected image light; and a beam splitter for: a) splitting a first portion of light arriving from an objective of a microscope and directing the first portion of the light arriving from an objective of the microscope toward the camera; b) transmitting a second portion of light arriving from the objective of the microscope and directing the second portion of the light arriving from an objective of the microscope toward at least one ocular of the microscope; and c) combining a portion of the projected image light generated by the digital image projector with the second portion of light arriving from the objective of the microscope such that the combination of the second portion of light arriving from the objective and the portion of the projected image light generated by the digital image projector is viewed through the at least one ocular of the microscope.

In some exemplary embodiments, the apparatus for image capturing and image projecting is configured to fit within a filter bay of the microscope.

In some exemplary embodiments, the apparatus further comprises at least one lens for focusing the first portion of light arriving from the objective of the microscope onto a digital imaging array of the digital camera.

In some exemplary embodiments, the apparatus further comprises further comprises at least one lens for focusing the projected image light generated by the digital image projector at the intermediate eyepiece image plane of the at least one ocular of the microscope such that the image projected by the digital image projector is in focus when viewed through the at least one ocular of the microscope.

In some exemplary embodiments, the beam splitter is configured to be placed at the Fourier plane of the microscope.

In some exemplary embodiments, the the apparatus for image capturing and image projecting is integrated within the at least one ocular of the microscope.

In some exemplary embodiments, the apparatus further comprises further comprises a shutter for blocking at least a portion of light arriving from the objective of the microscope such that a portion of the optical image of an object in front of the objective of the microscope is darkened so as to increase the visibility of the projected image light generated by the digital image projector when viewed via the at least one ocular.

According to another aspect of the present disclosed subject matter, a system for image capturing and image projecting is provided, the system comprising: an optical microscope having at least one objective and at least one ocular; an image capturing and image projecting unit positioned in the optical path between the at least one objective and the at least one ocular, the image capturing and image projecting unit comprises: a digital camera for capturing digital images; a digital image projector for generating projected image light; and a beam splitter for: a) splitting a first portion of light arriving from an objective of a microscope and directing the first portion of the light arriving from an objective of the microscope toward the camera; b) transmitting a second portion of light arriving from the objective of the microscope and directing the second portion of the light arriving from an objective of the microscope toward at least one ocular of the microscope; and c) combining a portion of the projected image light generated by the digital image projector with the second portion of light arriving from the objective of the microscope such that the combination of the second portion of light arriving from the objective and the portion of the projected image light generated by the digital image projector is viewed through the at least one ocular of the microscope; and a data processing unit for receiving and storing digital images captured by the digital camera, and generating digital images to be projected by the digital image projector.

In some exemplary embodiments, the system further comprises further comprises at least one human interface device such as a keyboard and a mouse, coupled to the data processing unit to enable entering data and commands by a user of the system for image capturing and image projecting.

In some exemplary embodiments, the system further comprises further comprises at least one remote server, coupled to the data processing unit to enable accumulating images and data from the data processing unit.

In some exemplary embodiments, the system further comprises further comprises at least one remote viewing station coupled to the data processing unit to enable remote viewing of images captured by the image capturing and image projecting unit.

In some exemplary embodiments, the at least one remote server or the at least one remote viewing station are coupled to the data processing unit via Internet.

In some exemplary embodiments, the system further comprises further comprises a slide camera for automatically identify the slide currently in front of the at least one objective.

In some exemplary embodiments, the slide camera captures an image of the slide currently in front of the at least one objective.

In some exemplary embodiments, the system further comprises further comprises: a plurality of objectives, each having different magnification, wherein a selected one of the plurality of objectives is in use; and an attachment for automatically identify which one of the plurality of objectives is currently in use, and report the magnification of the selected one of the plurality of objectives which is currently in use to the data processing unit.

In some exemplary embodiments, the digital image projector projects calibrated scale to be viewed with the optical image of the object in front of the selected objective currently in use, wherein the calibrated scale is based on the magnification of the selected one of the plurality of objectives which is currently in use which was reported to the data processing unit by the attachment for automatically identify which one of the plurality of objectives is currently in use.

In some exemplary embodiments, the user of the system for image capturing and image projecting is able to use the mouse to project markers onto the image seen via the at least one ocular.

In some exemplary embodiments, the user of the system for image capturing and image projecting is able to perform calibrated size measurement between two locations on the optical image viewed via the at least one ocular, wherein the calibrated measurement is based on the magnification of the selected one of the plurality of objectives which is currently in use which was reported to the data processing unit by the attachment for automatically identify which one of the plurality of objectives is currently in use.

In some exemplary embodiments, the apparatus further comprises further comprises a gaze follower integrated into at least one of the oculars for enabling system for image capturing and image projecting to follow and determine the place in the field of view that the user is attentive to.

In some exemplary embodiments, the system for image capturing and image projecting automatically stores and label the image captured by the digital camera if the place in the field of view that the user is attentive to remains stationary for duration longer that a preset threshold duration.

In some exemplary embodiments, the projected image generated by the digital image projector and viewed through the at least one ocular of the microscope comprises stored images captured by a system for image capturing and image projecting.

In some exemplary embodiments, the projected image generated by the digital image projector and viewed through the at least one ocular of the microscope comprises alphanumerical markings.

According to yet another aspect of the present disclosed subject matter, a method for image capturing and image projecting is provided, the method comprising:

viewing via at least one ocular a microscopically enlarged optical image of an object using an optical microscope; and concurrently viewing a projected digital image via the same the least one ocular.

In some exemplary embodiments, the projected digital image is at least partially overplayed the microscopically enlarged optical image.

In some exemplary embodiments, the method further comprises further comprises: capturing the microscopically enlarged optical image by a digital camera; and storing in a data repository a digital copy of the image captured by the digital camera.

In some exemplary embodiments, the projected digital image comprises an image stored in the data repository.

In some exemplary embodiments, the method further comprises digitally transmitting an image captured by the digital camera to a remote viewing station.

In some exemplary embodiments, the method further comprises digitally transmitting the projected digital image to the remote viewing station.

In some exemplary embodiments, the viewer using the remote viewing station and the user viewing via at least one ocular a microscopically enlarged optical image are both capable of sharing, manipulating and interacting with the projected digital image.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Unless marked as background or art, any information disclosed herein may be viewed as being part of the current invention or its embodiments.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 4A(ii) schematically depicts some details of an image capture and projection unit according to another exemplary embodiment of the current invention.

FIGS. 4C and 4D show the illumination of the partially vignette optical field of view.

FIG. 5A schematically shows optical paths for the slide image and digital overlay implemented in one eyepiece of the eyepieces pair.

FIG. 5B schematically shows the optical path for infrared illumination using LED or other light source and the detected image of the pupil area of eye on the imaging array using the pupil imaging optics on the second eyepiece.

FIG. 6 schematically shows a typical conventional microscope as known in the art.

FIG. 7 schematically shows a modified microscope having modified optics to enable vertical shift of the eyepiece intermediate image plane according to an exemplary embodiment of the current invention.

DETAILED DESCRIPTION

Figure 1:
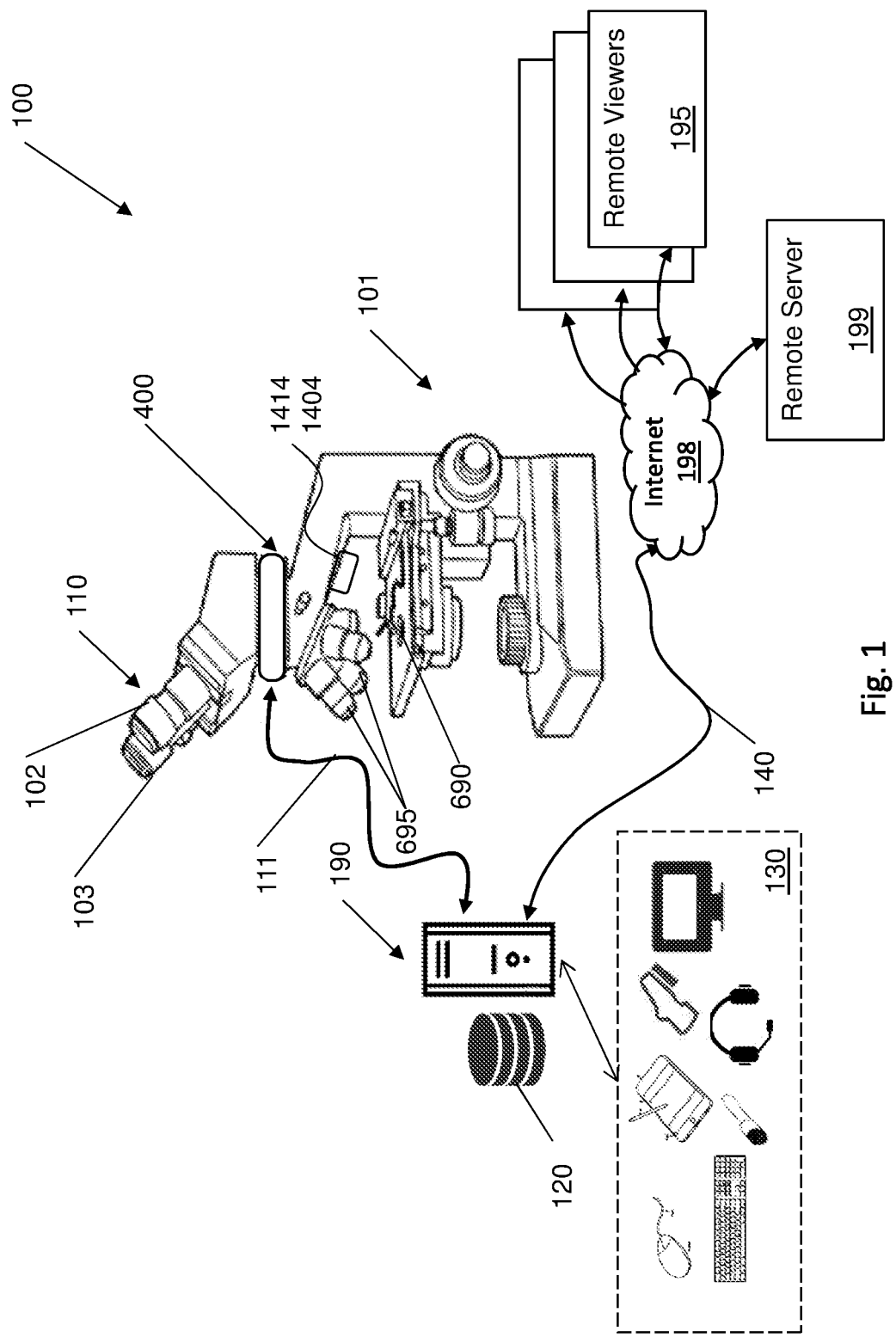
FIG. 1 schematically depicts a block diagram illustrating a system for display and capture of data according to an exemplary embodiment of the current invention.

Before explaining at least one embodiment of the invention in detail, it is to be understood that the invention is not necessarily limited in its application to the details set forth in the following description or exemplified by the examples. The invention is capable of other embodiments or of being practiced or carried out in various ways.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

In discussion of the various figures described herein below, like numbers refer to like parts. The drawings may not be to scale. For clarity, non-essential elements may have been omitted from some of the drawing.

To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, or the like) or multiple pieces of hardware.

Similarly, programs may be stand-alone programs, may be incorporated as subroutines in an operating system, may be functions in an installed software package, and the like.

It should be noted that the optical trains as seen for example in FIGS. 4B, 5A, 5B, 6 and 7 are schematic illustrations and optical components such as beam splitters (for splitting the light to two eyes, or to a camera port), image rotators or folding mirrors and prisms, irises or other components may not be seen in these figures to reduce clutter in the figures.

FIG. 1 schematically depicts a block diagram illustrating a system 100 for display and capture of data according to an exemplary embodiment of the current invention.

System 100 comprises a microscope 101 having an image display and capture unit 110 located within one or both of the microscope eyepieces 102/103 connected via wired or wireless communication 111 with a data processing unit 190.

Optionally, display and capture unit 110 has a form factor allowing it to replace a standard eyepiece of a microscope.

However, it should be noted that the entire or parts of the image display and capture unit may be integrated into, or added to microscope 101 in other locations for example Fourier plane image capture and projection unit 400 integrated or inserted in the optical accessory bay of microscope 101. More details will be seen in FIG. 2.

Optional attachment 1404 may be used to automatically identify which one of a plurality of objectives 695 is currently in use. Knowing the type of objective allows the system to have true calibration of the dimensions of object seen.

Optional attachment 1414, for example slide camera may be used to automatically identify the slide 690 currently in use. Optionally, attachment 1414 further records an image of the slide 690, optionally showing which specimen 459 is being viewed, or which part of a specimen is in the field of view.

As an example of how human interface devices 130 may work, a user may press a foot pedal for activating options of the system 100 such as capturing, selecting or saving an image, etc. Similarly, a microphone (e.g. in a headset) may be use for data entering (as voice record), or as text derived from the voice (via voice recognition software), or for entering voice commands.

In some cases, object viewed, and/or material generated by a data processing unit 190 and/or material stored by data repository 120, and/or material generated via human interface devices 130, may be viewed by user while looking through the eyepiece 102/103.

For example, but not limited to, the system 100 allows simultaneously comparing digital images similar to the specimen now viewed. This image may be stored in the data repository 120 and/or combined with other data collected or generated during said process, for example, but not limited to combining a video recording of the object being viewed, with material generated by one of the above or below mentioned means, for example, but not limited to metrics or notes.

In some cases, human interface device 130, may be used to generate material and/or commands, such as, but not limited to measurements of distance between multiple points on the image, notes, sending data via a data transmitting service for example: email, recordings including but not limited to voice, snapshots and video, that can be transmitted to data repository 120 via a communication channel 140.

Another aspect of the present invention is providing the ability to remotely communicate histological images with sufficient quality to allow peer review, consultation or reporting of the results. To enable the above, the microscope field of view, as observed by the microscope operator either visually through the eyepieces with or without digital overlay, or through a digital images captured or streamed by the image sensor viewable on the computer screen, can be transferred to another operator or remote viewer 195 connected to the system using a specific viewer software capable of receiving and displaying the above images or video.

The communication channel 140 allows transfer of both full resolution images at frame rates allowed by the available bandwidth and partial resolution video with frame rate sufficient to provide a dynamic response feeling for the remote viewer typically ranging between 5 to 20 frames per second. In this case, the video resolution is derived from the required video frames rate and available communication bandwidth. In case of a transmission of a static image, a full resolution image is transferred regardless the available bandwidth.

In addition to 2D images or video, an image overlay data such as marking shapes, arrows, text and magnification dependent calibration factor from image pixels to physical dimensions may also be transferred. The overlay data may be transferred in both directions: from the system to the remote viewers 195 and vice versa for allowing both the local and remote viewer to markup the image and perform measurements which are made visible to the microscope system operator and all remote viewers 195. This optional bidirectional communication allows interactive remote viewing and collaborative work of the local and the remote viewer or a plurality of viewers in real time.

For example, the remote viewer may be a surgeon viewing pathology slides being looked at by a pathologist or a technician, during surgery. This may allow the surgeon to make decisions such as extracting diseased tissue identified by a pathologist from a biopsy sample.

An expert, acting as a remote viewer 195, may be in voice communication with the user of microscope 101 and prompt the user to move the slide so as to view a specific area. Such expert, acting as a remote viewer 195, may use his pointing device at his remote viewing station, to point to the user a point of interest, by transmitting pointer data which is overlaid on the optical image seen on computer screen and/or within microscope eyepiece 102/103. Similarly, the remote viewer may mark the image or add notes to the image captured by microscope 101 and stored at data repository 120.

The use of the internet 198 as communication channel 140 allows remote viewing on a plurality of remote viewing stations and using a variety of type of viewing stations such as mobile smartphones, tablets, PC, smart TV and the likes.

It should be noted that current practice and some FDA rules mandate that human diagnostic work has to be performed from the optical image. Thus, the user at microscope 101 is the person making the diagnosis, and the remote viewer 195 may only advise and consult with him. However, in non-human research, or in research not involving human treatment (e.g. forensic studies) or if rules would change, the remote viewer may be the expert making the decision, while the user of microscope 101 may be a trained technician or a junior staff member. This type of operation may save time and cost by reducing the need to have the samples mailed to the expert, or the expert having to travel to the site where research is made.

Information captured by image capture and projection unit 110 or 400 may be stored in some cases in a data repository 120 (e.g. a database, a storage system, a memory including Read Only Memory—ROM, Random Access Memory—RAM, or any other type of memory, etc.), configured to store data (and enable retrieval and/or deletion and/or update thereof).

Data processing unit 190 may be connected via a communication channel 140 such as LAN, WAN or the Internet to a remote server 199.

Data processing unit 190 may be a general purpose computer such as a PC, a laptop or a tablet computer, or may be a dedicated proprietary data processor. Optionally, data processing unit 190 comprises a computer connected to input or output human interface devices 130 such as mouse, keyboard, touchscreen or touchpad, microphone speaker, earphone, headset, foot pedal, and/or screen. Although the user's work may be primarily performed while gazing at the optical image via the microscope, the user may use the mouse or other input devices, and see the effect of his input on the projected image without removing his eyes from the microscope eyepiece 102/103 as will be seen in FIG. 3 and later figures.

Figure 2:
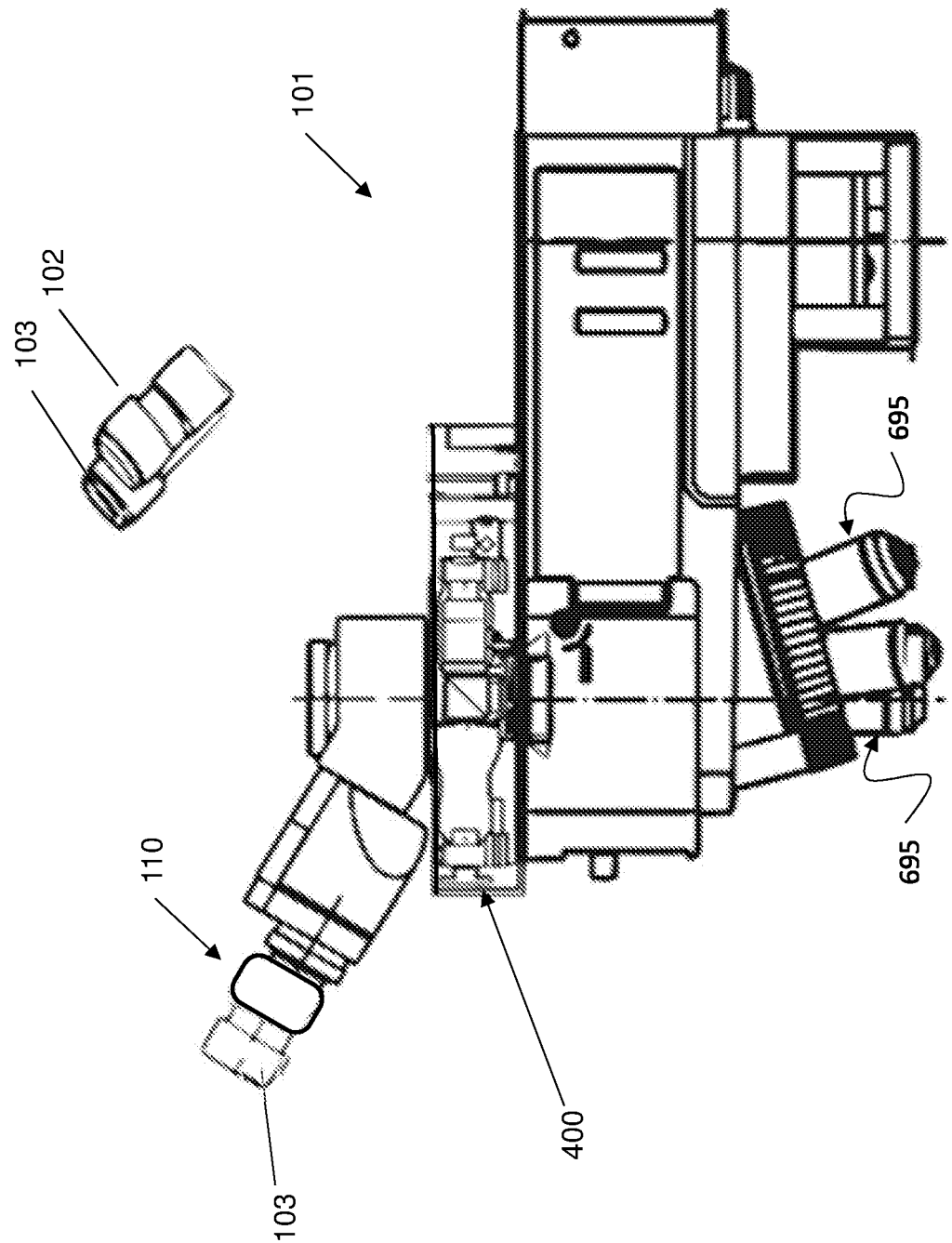
FIG. 2 schematically depicts a partial view of a microscope adapted for display and capture of data, illustrating optional locations for image capture and/or projection unit within a microscope according to an exemplary embodiment of the current invention.

FIG. 2 schematically depicts a partial view of a microscope 101 adapted for display and capture of data illustrating optional locations for image capture and projection units 110 and 400 within a microscope 101 according to an exemplary embodiment of the current invention.

Microscope 101 is adapted for display and capture of data by integrating into the microscope, at least one image display and capture unit 110, or a Fourier plane image capture and projection unit 400.

Optionally Fourier plane image capture and projection unit 400 has a form factor allowing it to fit into a standard optical accessory bay of a microscope.

Figure 3:
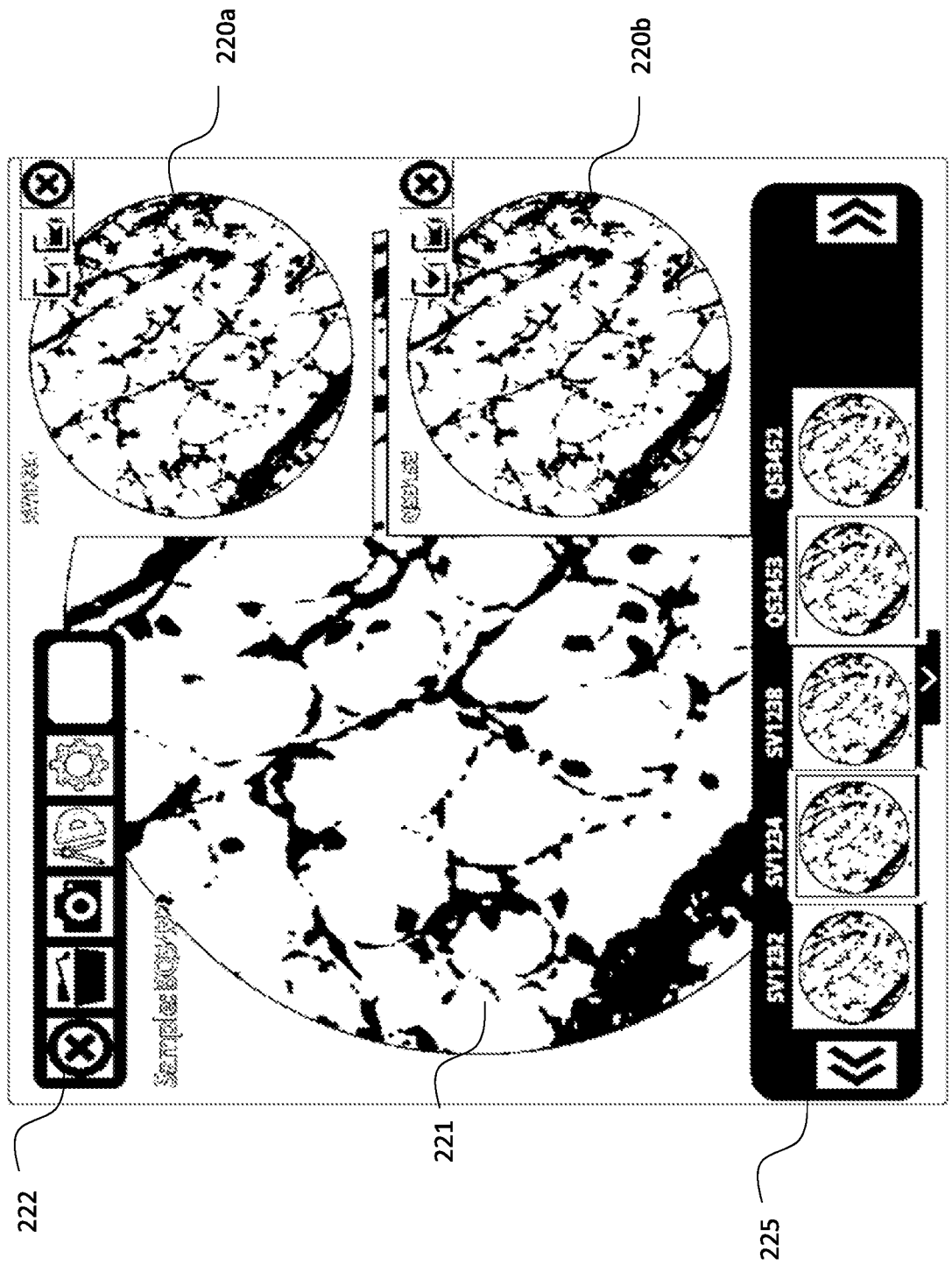
FIG. 3 shows the optical and digital overlay image visible to the observer through the microscope eyepiece according to exemplary embodiment of the current invention.

FIG. 3 shows the optical and digital overlay image visible to the observer through the microscope eyepiece according to exemplary embodiment of the current invention.

On top of the optical image 221 of the examined slide, a toolbar 222 is projected with functions such as but not limited to: a) take and save the digital image, b) retrieve digital image, c) draw and perform a dimensional measurement of a geometric form, d) generate a report based on a preset template and acquired images, etc.

An optional feature of the system is its ability to display a stored image or images 220a and optional 220b to enable comparison with the current optical image. Optionally, user selects the desired stored image from a list 225 of names, icons or small representations of stored images. Stored images may be images captured by the user, or another user on the same or similar device. Alternatively, stored images may be images captured by other means or generated by other means.

Figure 4A:
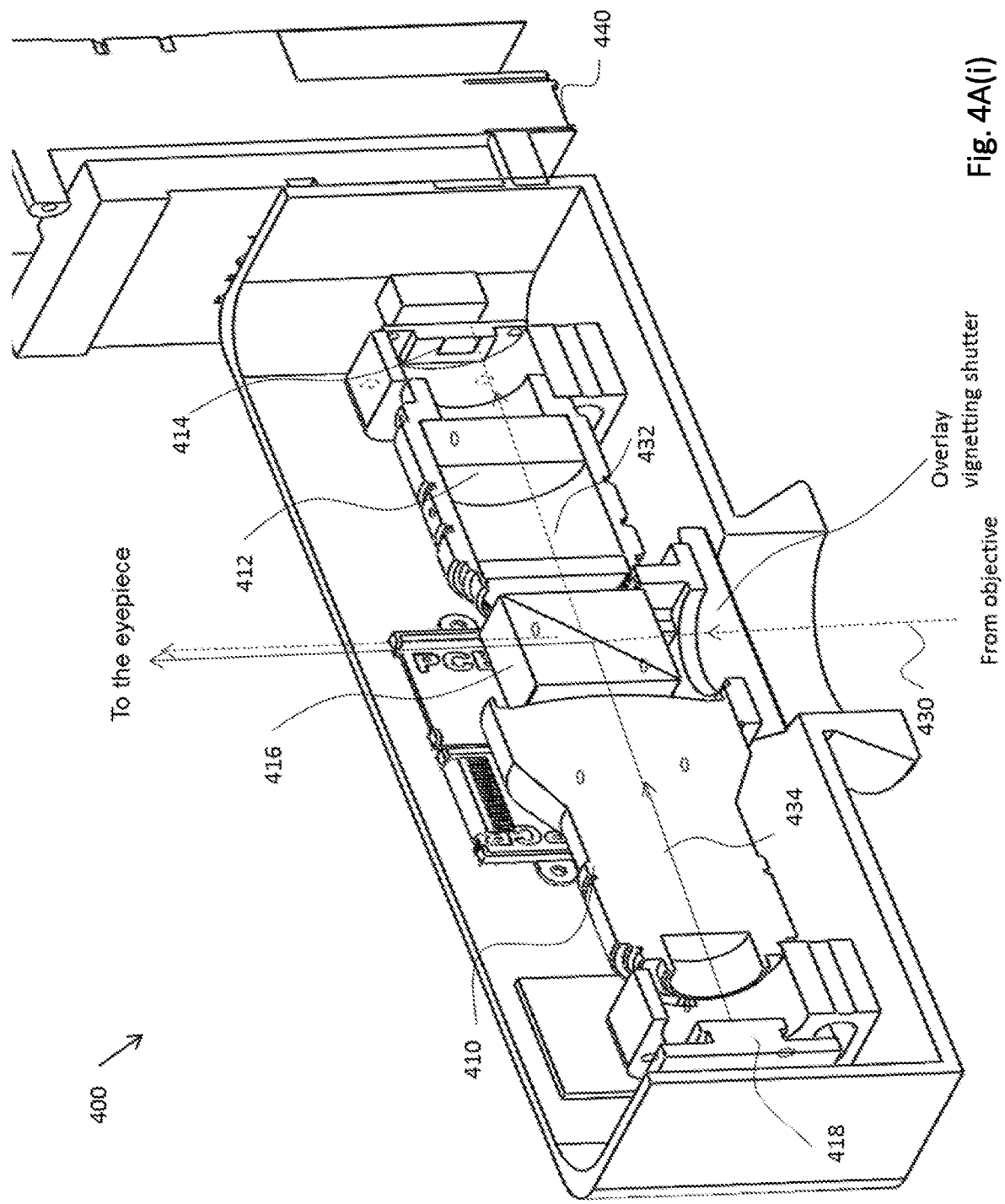
FIG. 4A(i) schematically depicts some details of an image capture and projection unit according to an exemplary embodiment of the current invention.

In order to enhance visibility of the stored image display, part of the optical field of view may optionally be vignetted by a mechanical shutter 570 (seen in FIGS. 4A(i), 4C, 4D, and 5D) movable by an actuation device such as a servo motor. Multiple configurations of vignette areas are achieved by using multiple regions on the shutter 570. Optionally shutter 570 is fully open when the full optical image is to be viewed.

Alternatively, darkening areas of the optical image may be done using an LCD display inserted within the optical train.

FIG. 4A(i) schematically depicts some details of an image capture and projection unit 400 according to another exemplary embodiment of the current invention.

In this arrangement, the Fourier plane image capture and projection unit 400 is located in a Fourier rather than intermediate image plane.

Projection lens sub-unit 410 and imaging lens sub-unit 412 are introduced between the imaging detector array 414 and the beam splitter 416, and between the micro-display 418 and the beam splitter 416. This arrangement allows greater freedom in physical dimensions of both micro-display 418 and the imaging detector array 414 by selecting the focal length of the lenses 410 and 412 in a way that both the imaging detector array and the micro-display cover the required portion of the field of view (FOV), preferably, most of the FOV, typically 22 or 26.5 mm in the eyepiece intermediate image plane.

Light from the objective 430 is split at beam splitter 416. A first fraction 432 of the Light from the objective 430 is directed to, and focused by the imaging optics 412 on the imaging detector array 414.

Projected light 434 from the micro-display 418 is brought by projection optics 410 to be at Fourier field at beam splitter 416, where it is combined with the light from the objective 430 and directed to the eyepiece.

Optionally, an electronics module 440 serves the micro-display and the imaging detector array 414. The electronics module 440 is generally in communication with host computer 190 (seen in FIG. 1). Alternatively, the host is integrated into the electronic module 440.

Preferably, the Fourier plane image capture and projection unit 400 has a form-factor that allows it to be inserted into the optical train of a standard microscope, for example in the filter's bay.

The imaging sensor location at the above described position has the advantage of increased field of view compared to standard "third ocular" location typically present on microscopes above the eyepieces. Due to longer path length to the imaging optics of the third ocular, the optical field of view at the third ocular is substantially vignetted compared to the FOV visible within the eyepiece. Remote viewer observing and interpreting the limited field of view image available using a camera at the third ocular port, lacks the same context perception as the microscope operator who observes the whole field of view. This may create a perceptual bias limiting the peer review quality because the peers are analyzing a substantially different data. Locating the imaging sensor close to the objectives does not limit the viewable field and is advantageous.

FIG. 4A(ii) schematically depicts some details of an image capture and projection unit 90 according to another exemplary embodiment of the current invention.

Image capture and projection unit 90 is similar in its function to image capture and projection unit 400 seen in FIG. 4A(i) but is more adopted in shape and size to be inserted into a optical accessory bay of a microscope.

For better understanding of this figure, the numbers of the equivalent elements in FIG. 4A(i) will be given within parenthesis. Image capture and projection unit 90 (400) is housed in an enclosure 91 having a form factor compatible with a optical accessory bay of a microscope. In housing 91 is beam splitter 92 (416) that splits the light 93 (430) coming from the objective and directs a portion of light 93 to be focused by lens assembly 94 (412) on a digital camera 95 (414).

Light from image projector 96 (418) is transformed to the Fourier plane by lens assembly 97a and 97b (serving the function of 410) and directed to beam splitter 92 (416) by two folding mirrors 98a and 98b [missing in the embodiment seen in FIG. 4A(i)].

Iris and filter assembly 99 [missing in the embodiment seen in FIG. 4A(i)] controls the light intensity before it enters lens assembly 97b and beam splitter 92 (416)

In many cases it is desirable to prevent the image projector 96 (418) light from being detected by the image sensor. In this case a pair of perpendicularly oriented polarizers are installed: one polarizer between the projector 96 and the beam splitter 92, while the second blocking polarizer between the beam splitter 92 and the image sensor 95 (414).

Figure 4B:
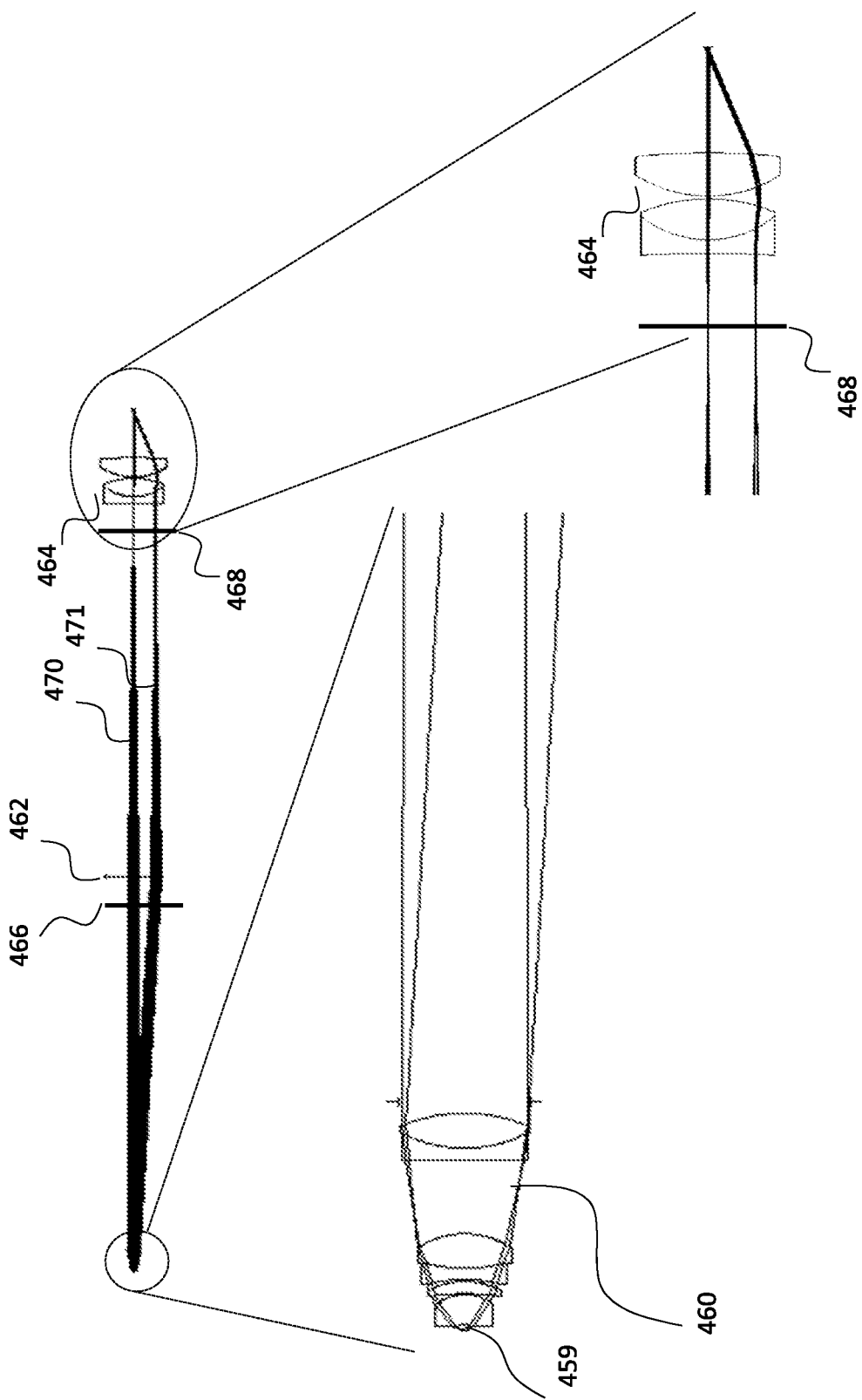
FIG. 4B schematically depicts the optical ray diagram demonstrating the ability to partially vignette the optical field before the tube lens.

FIG. 4B schematically depicts the optical rays diagram from the sample 459 through the infinity corrected objective 460, tube lens 462, intermediate eyepiece image plane 468 and to the eyepiece 464. The image shows the spatial separation of rays originated from a different sample points enabling the vignetting shutter 466 located in vicinity of a Fourier plane to selectively vignette part of the field of view rather than dim it as a whole.

FIG. 4C shows an example of a vignetted optical image 499 showing a darkened area 498 on, allowing highly visible overlay 49, icons of a digital image or data on optical image of the sample.

FIG. 4D schematically shows an exemplary graph 496 of the light intensity of the vignetted optical image 499.

FIGS. 5A and 5B schematically show an eyepiece combined system for optical determination of the observer eye line of sight according to exemplary embodiments of the current invention.

Optionally, a gaze follower is integrated into at least one of the eyepieces (FIG. 5B) for enabling system 100 to follow and determine the place in the field of view that the user is attentive to. Gaze following information may be used, as will be discussed later, to capture, select and/or store captured images.

FIG. 5A schematically shows optical paths for the slide image capture and digital overlay implemented in one eyepiece of the eyepieces pair.

Figure 5C:
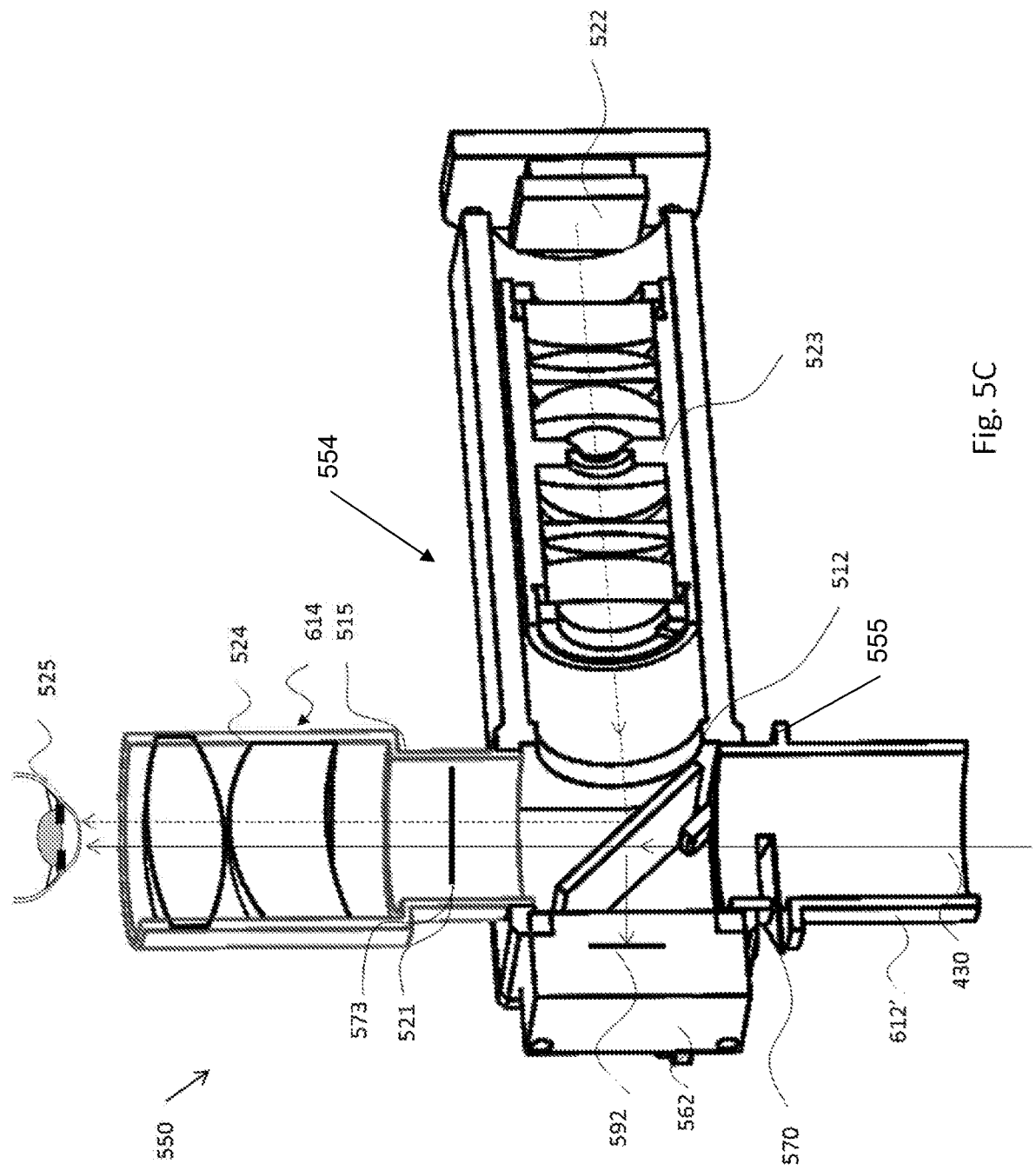
FIG. 5C schematically depicts a cross sectional view of a modified microscope eyepiece, showing one alternative implementation of the system to be integrated as a replacement of the one or more standard eyepieces of an infinity corrected microscope.

More details and schematic exemplary mechanical design are given in FIG. 5C and the associated text.

Light incoming from the objective, passes the tube lens and is split by beam splitter 512.

The imaging array 592 is located at the beam splitter conjugate location of the intermediate image plane 521.

Micro-projection technology micro display 522 is positioned on the other side of the beam splitter's conjugate intermediate image plane through relay optics 523. The eyepiece optics 524 is positioned such that the intermediate image plane 521 and its micro-display conjugate are projected to the observer's eye 525.

FIG. 5B schematically shows the optical path for Infra-Red (IR) illumination using LED 599 or other light source and the detected image of the pupil area of eye on the imaging array 598 using the pupil imaging optics 597 on the second eyepiece. Second beam slitter 512' is designed to deflect the IR illumination.

Figure 5D:
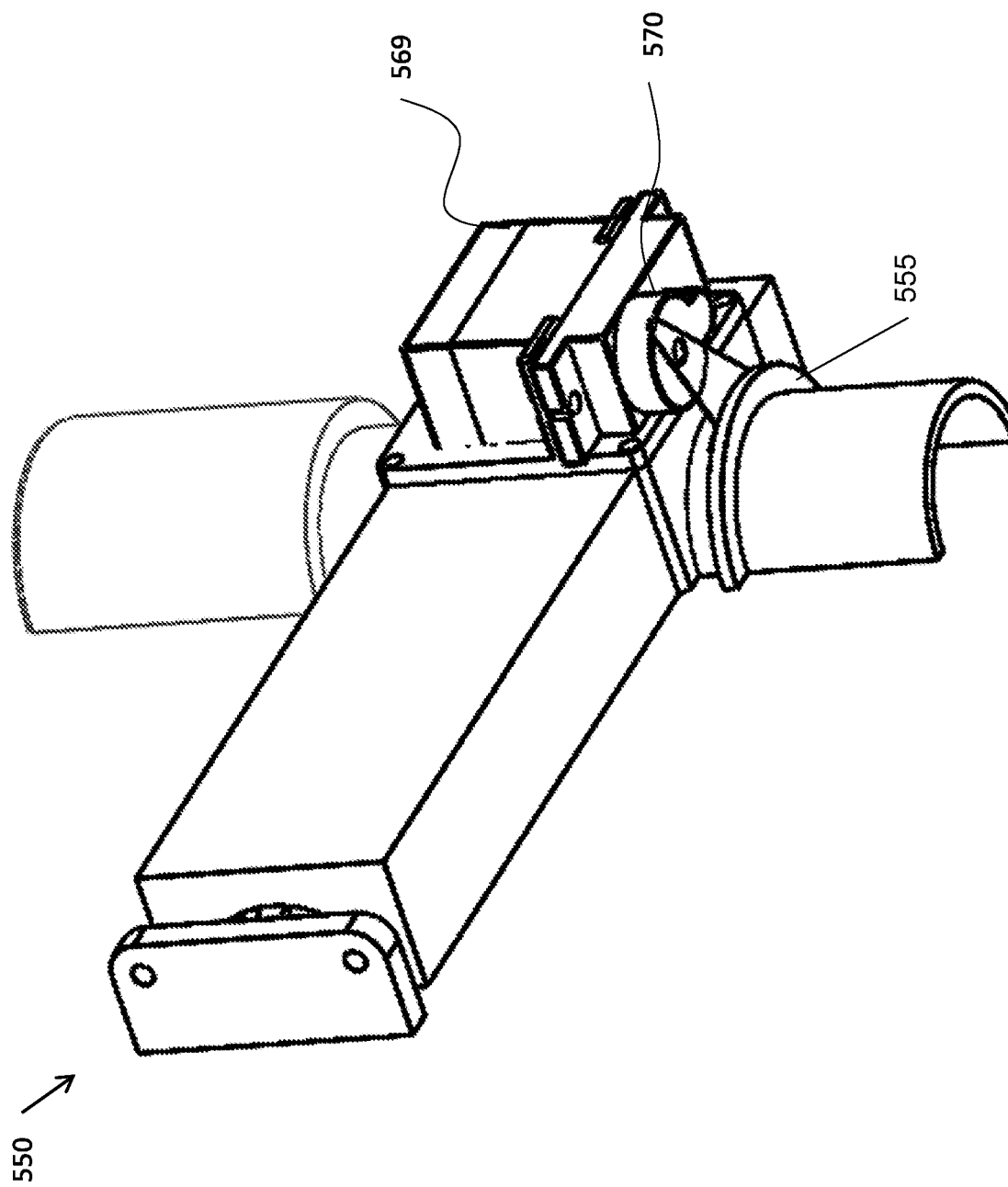
FIG. 5D schematically depicts a partial view of a modified microscope eyepiece, showing the overlay vignetting shutter and a servo motor actuating it.

FIGS. 5C and 5D schematically depict a cross sectional and side view respectively of a modified microscope eyepiece 550 according to exemplary embodiment to the current invention.

FIG. 5C schematically depicts a cross sectional view of a modified microscope eyepiece 550 showing one alternative implementation of the system to be integrated as a replacement of the one or more standard eyepieces of an infinity corrected microscope.

Light incoming from the objective 430 is split by beam splitter 512 with for example, a typical ratio of 90%/10% between the observer and the digital imaging device 562 respectively.

The imaging array 592 in imaging device 562 is located at the beam splitter conjugate location of the intermediate image plane 521. The physical dimensions of the imaging device preferably cover all or at least a substantial portion of the field of view, which is typically about 20 mm to 27 mm in diameter.

LCD, LCOS, AMOLED, TFT, DLP or other suitable microprojection technology micro display 522 is positioned on the other side of the beam splitter's conjugate intermediate image plane through relay optics 523. The eyepiece optics 524 is positioned such as the intermediate image plane 521 and its micro-display conjugate are projected to the observer's eye 525.

Alternatively, the imaging array 592 and micro-display 522 can be separately integrated on different eyepieces.

Optionally, modified microscope eyepiece 550 comprises a standard microscope eyepiece 614 and imaging and projection unit 554, such that different eyepieces 614 can be used with the same imaging and projection unit 554. Optionally, the eyepiece mounting tube 515 of standard microscope eyepiece 614 is shortened.

The imaging and projection unit 554 preferably comprises a mounting tube 612' having a standard diameter, and preferably fitted with a stopper 555 so it can be inserted into a standard microscope tube and descend to the level of the eyepiece mechanical reference plane 624 as seen in FIGS. 6 and 7 below.

In order to better view the projected image, the modified microscope eyepiece 550 may comprise an overlay vignetting shutter 570 which can be inserted into the light incoming from the objective 430, thus darkening a portion of the field of view. The overlay vignetting shutter 570 is actuated, for example manually, but preferably electronically such as by an electrical motor or solenoid 569. Optionally, overlay vignetting shutter 570 is automatically actuated when the user selects to view some overlay information of image such as retrieved digital image 220, toolbar 222, and/or other information (seen in FIG. 3).

In order to enhance visibility of the stored image display, part of the optical field of view may be vignetted (see FIGS. 4C and 4D) by a mechanical shutter 565 movable by an actuation device such as a servo motor 569. Multiple configurations of vignette areas are achieved by using multiple regions on the shutter. Optionally the motor 569 and shutter 570 are within a cover to prevent dust and other contaminants from entering the optics.

In some embodiments, micro-display 522 is replaced with a transparent micro display 573, positioned at the intermediate image plane 521. In this case, beam splitter 512 may be missing (unless needed for the image capturing).

Note that in the depicted example, the vignetting shutter 570 is not exactly in focal plane 521, and thus, the border of the darkened area 498 is not sharp, as can be seen in FIGS. 4C and 4D. This can be an advantage as it produces a smooth transition from the two parts of the image.

For example, Fourier plane image capture and projection unit 400 (seen in FIGS. 1, 2 and 4A(i)) may be used for image capturing only, while a modified eyepiece having a transparent micro-display is used for image projecting only. It should be noted that a modified eyepiece having a transparent micro-display may be made smaller as it has no beam splitter and may optionally be made with a form factor of a standard eyepiece.

FIG. 5D schematically depicts a partial view of a modified microscope eyepiece 550 showing the overlay vignetting shutter 570 and a servo motor 569 actuating it.

Optionally, the penetration of vignetting shutter 570 into the light from the objective 430, and thus the part of the FOV obstructed and darkened by it is controlled by the servo motor 569 according to the size of the projected image. Optionally, markers, icons and textual data are projected without actuating the overlay vignetting shutter 570, and stored image or images (such as 220a and/or 220b) are projected while actuating the overlay vignetting shutter 570.

FIG. 6 schematically shows a typical conventional microscope 600 as known in the art.

The eyepiece intermediate image plane 610 is located inside the mounting tube 612 of eyepiece 614, providing a very limited physical space for integration of components required for image acquisition and display data optical overlay. Typically, eyepiece 614 is affixed to the microscope 600 by inserting the eyepiece mounting tube 612 into the microscope tube 620. It should be noted that often the microscope tube 620 is folded and may comprise additional mechanical and/or optical elements. Generally, eyepieces are interchangeable, and are designed to be inserted such that they rest against the Eyepiece mechanical reference plane 622 at the end 624 of the microscope tube 620.

FIG. 7 schematically shows a modified microscope 650 having modified optics to enable vertical shift of the eyepiece intermediate image plane 654 according to the current invention.

To increase the available physical space, the modified intermediate image plane 660 was shifted upwards.

The standard eyepiece parfocal distance 618 is 10 mm, the field size is typically 20 to 27 mm. Thus an upward shift 658 of the intermediate image plane 654 by approximately 30 mm to 40 mm allows 20 mm to 30 mm of physical space to adequately integrate the necessary elements into a modified eyepiece 664 as shown in FIG. 6B. Image overlay components unit 668 can be located substantially above and outside the microscope tube 620. Thus, optionally and preferably, no modifications are done to the body of the microscope.

One simple way to provide such a shift of the eyepiece intermediate image plane 610 to its new location 660 is to shorten the distance from the sample slide 690 to the objective 695 from the initial distance 691 to the shorter value 692 by inserting a focus shift adaptor 693 between the objective mechanical reference plane 694 and the objective 695.

Example optical ray tracing calculations show negligible performance degradation while refocusing a 40× magnification objective with 180 mm tube lens by 16 micron in order to shift the intermediate image plane by 30 mm.

In order to provide the ability to instantly change between objectives with different magnifications without the need to refocus the sample, the distance between the sample and the objective mounting plane (the objective parfocal distance 697) is set constant regardless of the objective magnification.

The required sample focal shift to achieve a certain shift of the eyepiece intermediate plane 619 depends on the objective magnification and thus refocusing the sample plane would be required while changing the objective to a different magnification. To eliminate the need for the sample refocusing, a focal shift adaptor 693 is introduced, tailored for each objective magnification that serves two purposes: provide a focal shift of the eyepiece intermediate image plane and maintain a constant objective parfocal distance regardless of the objective magnification.

It should be noted that the use of a Fourier plane image capture and projection unit 400 may be preferred to using modified microscope eyepiece 550 for the following reasons: a) it require minimal or no changes of the microscope. In contrast the microscope eyepiece 550 may be cumbersome as the eyepiece is moved from the ergonomically design location. b) Some microscope vendors such as in Olympus microscope, the oculars are non-standard and it is difficult to adopt a modified microscope eyepiece 550 for it.

Figure 8:
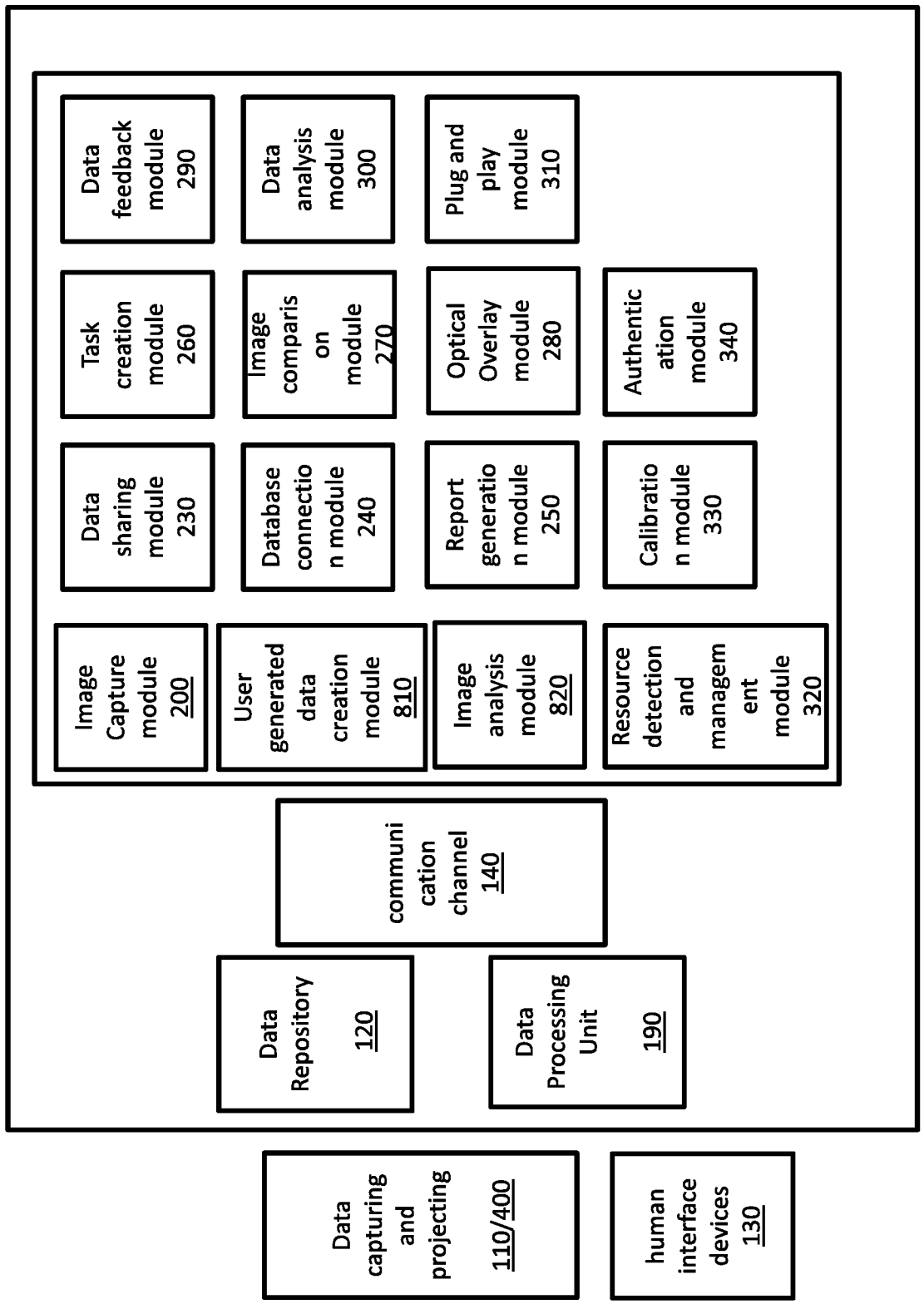
FIG. 8 schematically depicts a block diagram showing some details of the system for image capturing and projecting, according to an exemplary embodiment of the current invention.

FIG. 8 schematically depicts a block diagram showing some details of the system for image capturing and projecting, according to the current invention.

With reference to FIG. 8, the data processing unit 190 comprises hardware modules, and/or can be configured to execute the following software modules: image capture module 200, user generated data creation module 810, image analysis module 820, resource detection and management module 320, data sharing module 230, database connection module 240, report generation module 250, calibration module 330, task creation module 260, image comparison module 270, optical overlay module 280, authentication module 340, data feedback module 290, a plug and play module 310.

According to some examples of the presently disclosed subject matter, image capture module 200 can be configured to continuously record signals from the image detector array (camera), including video and/or stills (e.g., snapshots), workflow, actions, and/or all, or part of, material as viewed from microscopic optic plane. The image capture module 200 may also be configured to collect images each time the user performs an action, such as, but not limited to stopping the scanning of the slide, or performing certain action with the user's eyes. The images recorded and/or still images can be saved to the data repository 120, and/or utilized by the data processing unit 190 for further analysis, and/or sent to a different location via the data sharing module 230.

According to some examples of the presently disclosed subject matter, some potential areas of interest could be determined by monitoring the operator gaze locking on a particular area while scanning the slide and searching for pathologies or anomalies. In such event of operator's gaze locks for more than a pre-defined period of time, ranging typically between 0.5 to 5 seconds, a camera image acquisition will be triggered. In case of a moving slide, the sensor image acquisition (integration) time required to obtain a reasonable quality image can be long enough to cause an image smear due to the slide motion. In this case, a flash of light illuminating the specimen may optionally be triggered. For example, the flash light could be a Xenon arc lamp or LED sources mechanically and optically integrated into the microscope illumination path of into the system described in the preset invention.

Optionally, areas that the operator gazed at for duration longer than the preset time are stored at higher resolution or image quality (for example using higher number of bits, or lower image compression, or no compression)

According to some examples of the presently disclosed subject matter, user generated data creation module 810 can be configured to receive input from the human interface device 130, and then to create data which will be overlaid utilizing the optical overlay module 280. As an example, but not limited to, this process can begin when the user chooses to measure distance between different points of the specimen being viewed via single ocular and/or multiple ocular device, and whereas the user clicks with a stylus or any other human interface device 130 on start point and dragging the human interface device 130 to an end point and clicking again whereas the data processing unit 190 utilizing the user generated data creation module 810 will calculate the distance using known methods and techniques (e.g. taking into account the magnification of the microscope).

Further examples of how the user generated data creation module 810 can be utilized by the user includes utilizing human interface device 130 to collect written notes, voice notes, receive commands of different images that the user may wish to see simultaneously while viewing the image in order to compare the images e.g., a specimen from the same patient from a previous point in time and/or a specimen from a different patient with a similar physical condition and/or any other relevant, similar characteristics, patient and/or specimen data, tasks or commands e.g. to other users, reminders, etc. Data created using the user generated data creation module 810 may be stored in the data repository 120 and or utilized by data processing unit 190 for further analysis, as an example, but not limited to, data created via the user generated data creation module 810 can be combined with data generated via the image capture module 200, and this combined image can be viewed at a later time, and/or by a different user in a different location.

According to some examples of the presently disclosed subject matter, image analysis module 820 can be configured to analyze parts of, or the entire image viewed. Based on these analysis techniques, image analysis module 820 can be configured to create new data which can dictate workflow, and/or be used by the user to form conclusions or diagnosis. As an example, but not limited to, the image analysis module 820 can determine which magnification (e.g., microscope objective) is presently being use, and this will have implications for the user and other modules, as an example, but not limited to, calculating metrics between multiple points on the specimen. A further example of the task performed by image analysis module 820 may include quantitative analysis of the specimen using known techniques. A further example of the task performed by image analysis module 820 is automatically detecting patterns in the specimen in order to determine characteristics using known techniques. A further example of the task performed by image analysis module 820 may be to automatically make adjustments to color, brightness and additional features of the image. A further example of the task performed by image analysis module 820 may be to leverage big data to determine if a diagnosis made by a user is an outlier, based on comparisons with similar datasets from users located in other locations. As an example, if a user found a tissue sample to be cancerous, but in the overwhelming majority of instances involving similar tissue samples other users found the specimen to not be cancerous, an alert may be activated to inform the user that the diagnosis is not in line with other users.

According to some examples of the presently disclosed subject matter, resource detection and management module 320 can be configured to monitor how much power is required, how much data storage may be used, and other issues related to continued functioning of the apparatus. The resource detection and management module 320 can determine if there is any malfunction of related software modules or hardware. Data generated by the resource detection and management module 320 can be displayed to user in the overlay image, or can be sent to a user's personal computing device (e.g., email alert).

According to some examples of the presently disclosed subject matter, data sharing module 230 can be configured to allow user to collaborate with other users in different locations by sending data, images, or other information relevant to what is being viewed by the user. As an example, but not limited to, the data sharing module 230 can command the user's file sharing protocol (i.e., email) to send data (as an example, but not limited to, the view of the image with or without the image overlay) via their email account. A further example may include data shared to another user's eyepiece or another monitor, such that the additional users can view in real time, or at a later time, the view of the first user from the image enhancement device, with or without the image overlay.

According to some examples of the presently disclosed subject matter, database connection module 240 can be configured to connect the data repository 120 with external data repositories, for example server 199, such as, but not limited to a Laboratory Management Information System (LIS), such that relevant information can be shared between the multiple data repositories. In some instances, data generated by the user will be transferred to the external data repository, and in other instances, data from the external repository will appear as part of the image overlay while the user is viewing the specimen. In some instances, the user's existing data repository can be used as the data repository 120, and in some instance the data repository 120 can be utilized by the user as a data repository for other data.

According to some examples of the presently disclosed subject matter, report generation module 250 can be configured to allow the user to generate a case report of the specimen being viewed while still viewing the specimen that will convey the diagnosis, conclusion, and/or decision of the user. As an example, the user may click on an icon that is displayed while viewing the image, such that the user can create a case report based on the images of the specimen viewed, based on metrics calculated, and based on images of similar specimens viewed. The user can add content to the report using human interface device 130, add images to the report and can save the report in the data repository 120. Reports generated can include images of specimen, patient details, notes of the user, a link to view additional images, a recorded image of the work performed by user, or a link to a web based location where additional patient data is available. Reports generated can be saved as well in external data repositories.

According to some examples of the presently disclosed subject matter, calibration module 330 can be configured to allow the user to calibrate the additional single eyepiece 90, and/or primary and/or existing eyepiece 102, and/or image display and capture unit 110, Fourier plane image capture and projection unit 400. This module makes use of technologies to determine correct calibration.

According to some examples of the presently disclosed subject matter, task creation module 260 can be configured to allow the user to assign tasks to oneself or to other users, e.g. via an icon or other command method. The task creation module 260 can optionally give alerts to the user. An example, but not limited to, of the task creation module is the user, after viewing the specimen, sends a note to a different user, requesting the second user to perform further analysis, as explained above.

According to some examples of the presently disclosed subject matter, image comparison module 270 can be configured to allow the user to access and view images from data repository 120, and allow user to compare the image with the specimen in real time. The image comparison module 270 can be controlled via commands of the human interface device 130 or icons on the image overlay. As an example, but not limited to, the user may look at a specimen of a patient with certain physical characteristics, and a specific type of tumor, and wish to compare this image with other specimens of the same tumor type and personal characteristics. A further example is the user may view a specimen, and compare to an older specimen of the same patient. A further example, but not limited to, can be in the case where the user is viewing specimens stained with kappa/lambda, such that there are two identical slices of the same specimen stained differently, and after viewing the first stain and capturing an image with the image acquisition module, can view the captured image and then switching slides in order to view both the captured image and second slide simultaneously.

According to some examples of the presently disclosed subject matter, authentication module 340 can be configured to allow the software to determine user identification, and determines the information to be displayed for this user.

According to some examples of the presently disclosed subject matter, optical overlay module 280 can be configured to create the overlay via one of the abovementioned image projection means. The overlay image may comprise one or few of: images, text, markers, data, and icons.

According to some examples of the presently disclosed subject matter, data feedback module 290 can be configured to allow user and or administrator to view work performed, statistics of work from different users, and to see reports based on this data.

According to some examples of the presently disclosed subject matter, data analysis module 300 can be configured to analyze data collected or created by user, as an example, but not limited to, data generated by user via human interface device 130 and/or received from the user generated data creation module 810. The data analysis module 300 can generate new data, and/or provide alerts based on the data collected. As an example, but not limited to, the data analysis module 300 may determine based on the calculation of the metrics measured by the user via the human interface device 130 that the specimen being viewed should be classified in a certain way. A further example can be that based on a combination of the image being viewed, and based on images from previous specimens of the same sample, that there is a change in the status of the patient. A further example may be that based on input from external sources (e.g. the oncologist of the patient) that additional considerations should be taken into account by the user, and these are based on techniques know to those fluent in the art.

A further example may be that based on the user moving the human interface device 130, the optical overlay module 280 should overlay new information for the user. A further example may be that based on the user clicking on an icon to share data, a command should be sent to an email program to share this data with the chosen location and/or new user.

According to some examples of the presently disclosed subject matter, plug and play module 310 can be configured to allow user to change the configuration of system 100. For example to install additional devices, such as additional eyepiece set 90, and/or eyepiece 102, or to switch on or off installed image capturing or image projection and/or other peripheral devices.

It is to be noted that, with reference to FIG. 8, some of the blocks can be integrated into a consolidated block or can be broken down to a few blocks and/or other blocks may be added. Furthermore, in some cases, the blocks can be performed in a different order than described herein (for example, block 310 can be performed before block 300, etc.). It is to be further noted that some of the blocks are optional. It should be also noted that whilst the flow diagram is described also with reference to the system elements that realizes them, this is by no means binding, and the blocks can be performed by elements other than those described herein.

Figure 9:
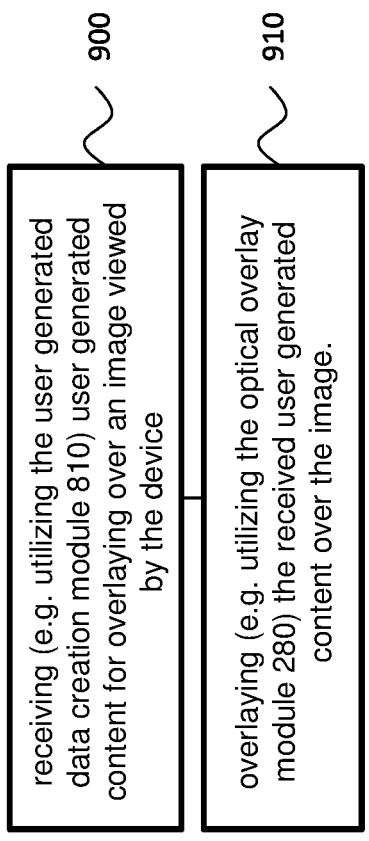
FIG. 9 schematically depicts a flowchart illustrating a sequence of operations for data overlay according to exemplary embodiment of the current invention.

FIG. 9 schematically depicts a flowchart illustrating a sequence of operations for data overlay according to exemplary embodiment of the current invention.

According to some examples of the presently disclosed subject matter, the user is viewing an image via microscope 101, and while viewing the specimen, the Data processing unit 190 can be configured to receive (e.g. utilizing the user generated data creation module 810) user generated content for overlaying over an image viewed by the device (step 900), and then overlay (e.g. utilizing the optical overlay module 280) the received user generated content over the image (step 910).

It is to be noted that, with reference to FIG. 9, some of the blocks can be integrated into a consolidated block or can be broken down to a few blocks and/or other blocks may be added. Furthermore, in some cases, the blocks can be performed in a different order than described herein (for example, block 910 can be performed before block 900, etc.). It is to be further noted that some of the blocks are optional. It should be also noted that whilst the flow diagram is described also with reference to the system elements that realizes them, this is by no means binding, and the blocks can be performed by elements other than those described herein.

Figure 10:
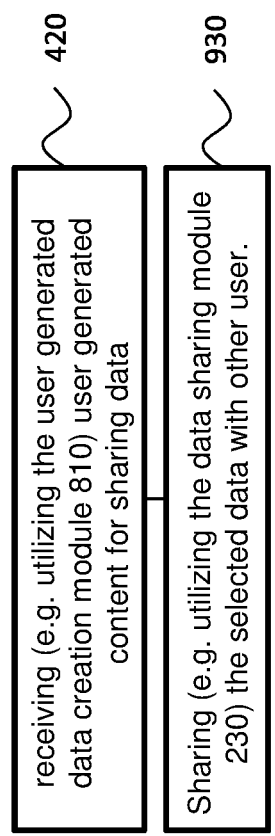
FIG. 10 schematically depicts a flowchart illustrating sequence of operations for sharing data according to exemplary embodiment of the current invention.

FIG. 10 schematically depicts a flowchart illustrating sequence of operations for sharing data according to exemplary embodiment of the current invention.

According to some examples of the presently disclosed subject matter, data in the data repository 120 and/or viewed by user may be shared with other users and/or locations.

The user may optionally decide on which data to share using human interface device 130 (e.g., mouse or stylus). It is noted that the user is not limited to sharing data while working on the microscope, but rather is able to share data from any location where the user has access to the data repository 120. As an example, but not limited to, is the user clicking on an image, and/or clicking on an icon describing what data to be shared. The data processing unit 190, may utilize user generated data creation module 810 and/or data sharing module 230, and may share the data with another user and/or location. Data shared with other users and or locations may be viewed in part and/or its entirety on the microscope, or computer screen, or any other device that allows for viewing of recorded images. The data repository 120 may be configured to receive all data generated by the user and/or data processing unit 190.

It is noted that the data repository 120 may receive data from external databases, and data processing unit 190 may use a module to overlay this data to the user, and subsequently, the user may choose to share this data with another user and/or location.

It is to be noted that, with reference to FIG. 10, some of the blocks can be integrated into a consolidated block or can be broken down to a few blocks and/or other blocks may be added. Furthermore, in some cases, the blocks can be performed in a different order than described herein (for example, block 930 can be performed before block 420, etc.). It is to be further noted that some of the blocks are optional. It should be also noted that whilst the flow diagram is described also with reference to the system elements that realizes them, this is by no means binding, and the blocks can be performed by elements other than those described herein.

Figure 11:
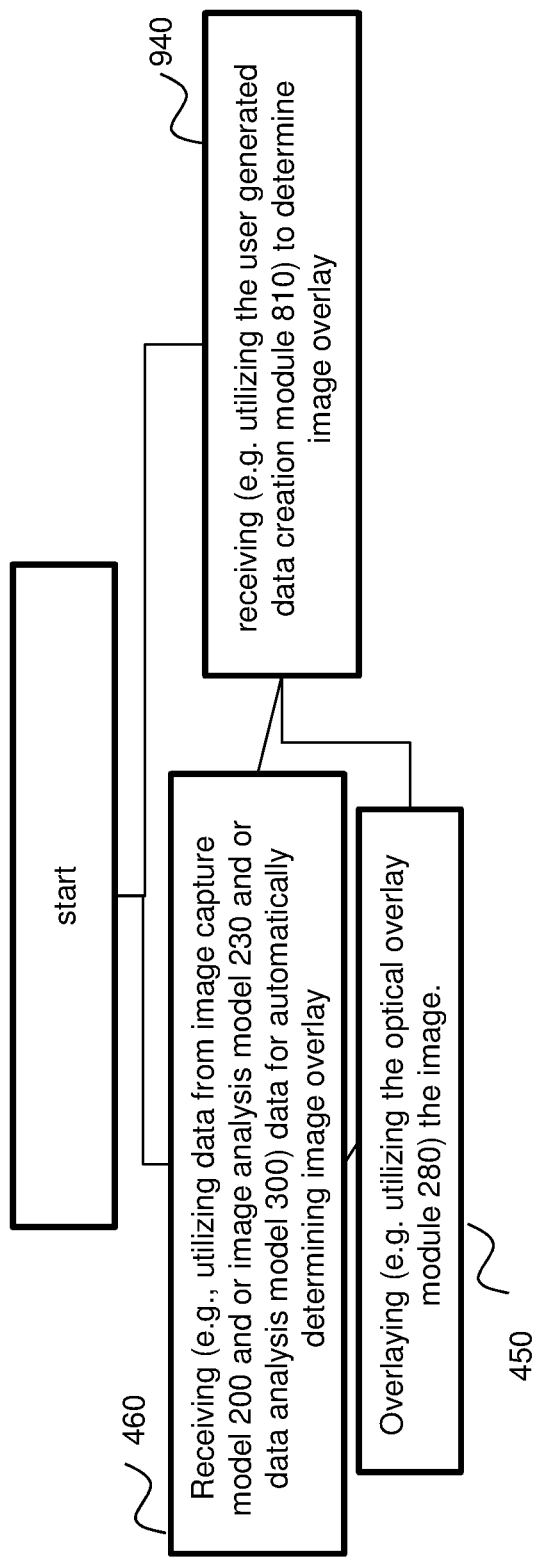
FIG. 11 schematically depicts a flowchart illustrating sequence of operations for image overlay according to exemplary embodiment of the current invention.

FIG. 11 schematically depicts a flowchart illustrating sequence of operations for image overlay according to exemplary embodiment of the current invention.

According to some examples of the presently disclosed subject matter, the user may view the specimen in the microscope, and the user may utilize an human interface device 130 (e.g., microphone, stylus, keyboard) to overlay, and/or select, and/or to change an image, and or data, and or icons and/or other information that the user wishes to view as an overlay. In the example that the user wishes to view an image as an overlay, the user generated data creation module 810 may receive data from human interface device 130, which may be utilized by the image comparison module 270 to select the appropriate image to overlay 940, and which may be utilized by the optical overlay module 280 to overlay this image 450. As a further example of overlaying an image, the data processing unit 190 may utilize the image capture module 200, and/or image analysis module 820 and/or data analysis module 300 to automatically decide on which image to display as an overlay 460. The data repository 120 may be configured to receive all data generated by the user and/or data processing unit 190.

According to some examples of the presently disclosed subject matter, the user may utilize human interface device 130 to write notes (e.g., on a keyboard and/or with a stylus pen) and/or draw lines, as example, but not limited to, lines that measure distance or circumference of points on the specimen, such that these lines will appear as an overlay with the distance calculated between the points. The user generated data creation module 810 may receive data from human interface device 130, and may utilize the optical overlay module 280 to have this data appear as an overlay for the user. The user may decide to keep the overlaid data, or may decide to no longer see the overlaid data or parts thereof, and as such, may utilize the human interface device 130 to change what is viewed in the overlay. It is stated that the processing unit 190 may utilize data from one or more of the modules, and generate data and/or measurements and/or comments and/or other data, and may utilize the optical overlay module 280 to project as an overlay for the user. An example of such, but not limited to, may be an alert or task for the user from another user and/or superior. The user may decide to keep or remove the overlay automatically generated by the processing unit 190 with a human interface device 130. The data repository 120 may be configured to receive all data generated by the user and/or data processing unit 190.

It is to be noted that, with reference to FIG. 11, some of the blocks can be integrated into a consolidated block or can be broken down to a few blocks and/or other blocks may be added. Furthermore, in some cases, the blocks can be performed in a different order than described herein (for example, block 450 can be performed before block 940, etc.). It is to be further noted that some of the blocks are optional. It should be also noted that whilst the flow diagram is described also with reference to the system elements that realizes them, this is by no means binding, and the blocks can be performed by elements other than those described herein.

Figure 12:
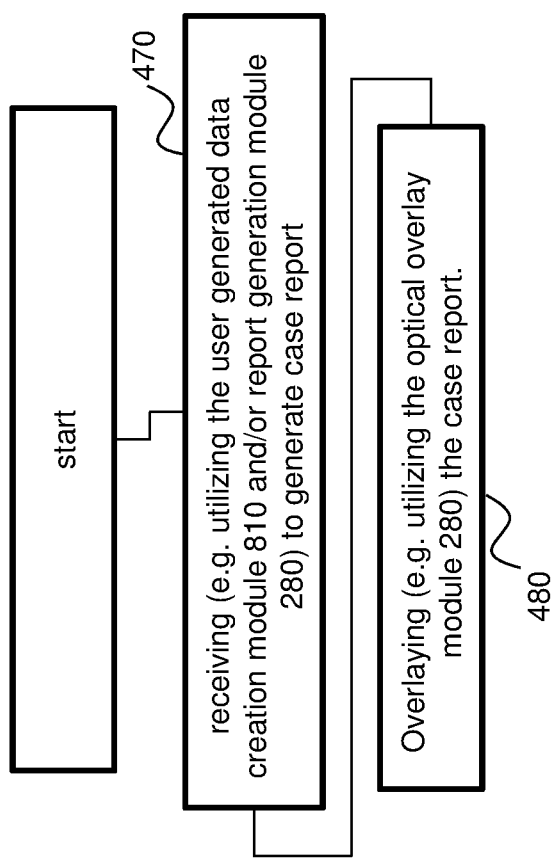
FIG. 12 schematically depicts a flowchart illustrating sequence of operations for case report generation according to exemplary embodiment of the current invention.

FIG. 12 schematically depicts a flowchart illustrating sequence of operations for case report generation according to exemplary embodiment of the current invention.

According to some examples of the presently disclosed subject matter, the user may choose to generate and/or update a case report which may contain images, specimen data, notes, and other information that may be chosen by the user. The user may utilize human interface device 130, and may for example, but not limited to, click on a report generation icon that is digitally displayed as an overlay overlaid within the eyepiece.

The user generated data creation module 810 may receive this command, and the report generation module 250 may collect relevant specimen data that may be received from database sharing module 240 470 and/or data created by user via human interface device 130 and/or images collected from image capture module 200 and may utilize optical overlay module 280 to overlay this report for the user.

User may make changes to report by utilizing human interface device 130. Furthermore, the data may be shared with another location (e.g., user's personal computer) where user may continue to make changes to report. The data repository 120 may be configured to receive all data generated by the user and/or data processing unit 190.

It is to be noted that, with reference to FIG. 12, some of the blocks can be integrated into a consolidated block or can be broken down to a few blocks and/or other blocks may be added. Furthermore, in some cases, the blocks can be performed in a different order than described herein (for example, block 480 can be performed before block 470, etc.). It is to be further noted that some of the blocks are optional. It should be also noted that whilst the flow diagram is described also with reference to the system elements that realizes them, this is by no means binding, and the blocks can be performed by elements other than those described herein.

Data associated with the image may comprise specimen details such as, but not limited to, test type, type of tissue, assigning physician, identification of hospital where biopsy was performed, time of biopsy etc., material automatically generated by data processing unit 190 such as, but not limited to, distance measurements, severity of specimen, marking or shading of specimen etc. patient details, for example, but not limited to, patient name, address, identification number, payment details, insurance etc., data from other databases such as, but not limited to, data that originated from a Laboratory Information System, voice recordings of user, tasks assigned by user such as, but not limited to, reminders to user, commands given by user to another user based on what was seen via the microscope.

In some cases, data repository 120 can be further configured to enable retrieval, update and deletion of the stored data. It is to be noted that in some cases, data repository 120 and/or data processing unit 190 can be located locally on user's computer, or any other suitable location. In some cases, data repository 120 and/or data processing unit 190 can be distributed between two or more locations. In some cases, additionally or alternatively, data repository 120 and/or data processing unit 190 can be shared between multiple computers.

Figure 13:
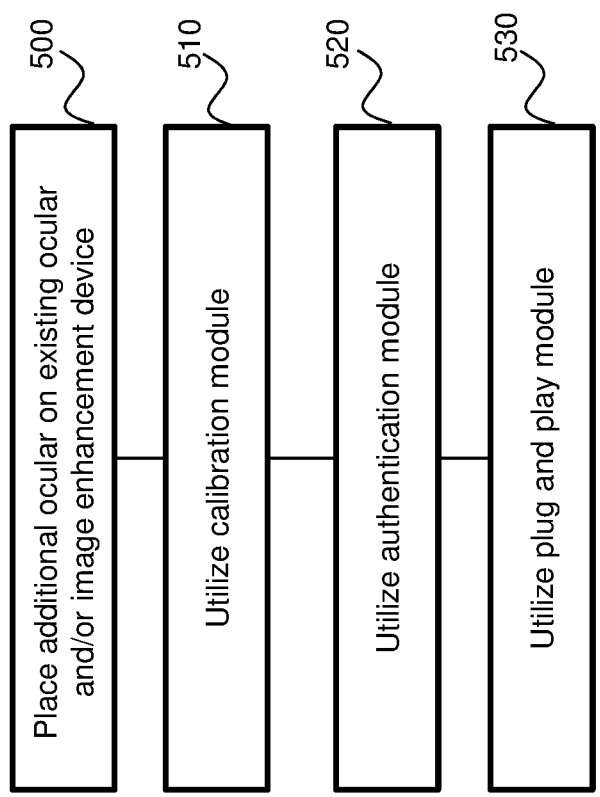
FIG. 13 schematically depicts a flowchart illustrating sequence of operations for connecting new hardware and setting it up according to exemplary embodiment of the current invention.

FIG. 13 schematically depicts a flowchart illustrating sequence of operations for connecting new hardware and setting it up according to exemplary embodiment of the current invention.

According to some examples of the presently disclosed subject matter, the described embodiment can be connected to the microscope, (step 500). Step 500 may be replaced by installing or turning on or connecting any other image capturing and projecting unit or units disclosed above for example Fourier plane image capture and projection unit 400, which is optionally plug and play compatible.

According to some examples of the presently disclosed subject matter, plug and play module 530 can be utilized to allow all abovementioned software modules to operate with newly added hardware. Data processing unit 190 can utilize calibration module 510 to determine that all hardware is aligned. Data processing unit 190 can utilize authentication module 520 to determine identity of user, and determine the appropriate data to be displayed on overlay.

It is to be noted that, with reference to FIG. 13, some of the blocks can be integrated into a consolidated block or can be broken down to a few blocks and/or other blocks may be added. Furthermore, in some cases, the blocks can be performed in a different order than described herein (for example, block 530 can be performed before block 520, etc.). It is to be further noted that some of the blocks are optional. It should be also noted that whilst the flow diagram is described also with reference to the system elements that realizes them, this is by no means binding, and the blocks can be performed by elements other than those described herein.

Dimensional measurements described in FIGS. 3 and 11 require calibration from camera pixels to physical length units, depending on the objective selected. In one embodiment, when changing the objective in use, the magnification factor is manually changed by the user using one of the human interface devices 130 every time the user changes the objective. This way of calibration changing is prone to human errors and an alternative embodiment with automatic magnification detection, described below is preferred.

Figure 14:
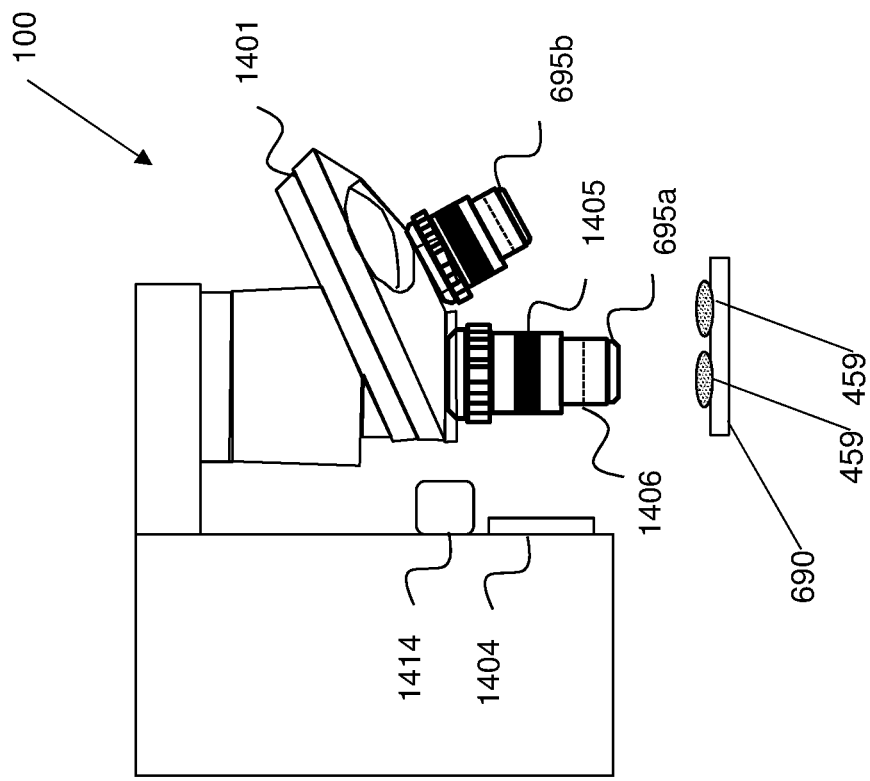
FIG. 14 schematically depicts an assembly for automatic identification of the objective magnification in use which is required for correct dimensional calibration of image measurements, according to exemplary embodiment of the current invention.

FIG. 14 schematically depicts a device and a method allowing the system 100 to calibrate the dimensional measurements automatically by selecting the preset calibration factor for each objective magnification. This may be done using a sensor 1404 capable of identifying distinct markers 1405 located on each objective such as objectives 695a and 695b. The sensor/marker combinations can be: RFID reader/RFID tag, 2D color image array/colored ring code 1406 on the objective, barcode reader/barcode on the objective or similar.

Alternatively yet, turret 1401 which rotates to exchange objectives, may be fitted with electro mechanical switches of sensors to indicate which objective is in use.

It should be noted that changing the eyepiece changes the magnification (and sometimes the observed field of view). However, since the image capturing and the image projection are done before the final eyepiece optics, the calibration remains.

Optional attachment 1414, for example slide camera may be used to automatically identify the slide 690 currently in use. A barcode or other markings on the slide may identify the slide and associate it with data in the database regarding it origin (for example patient name, organ, location, biopsy number etc.). The image of the slide, and the slide ID are thus associated with microscopic images taken, thus preventing errors. Optionally OCR (Optical Character Recognition) software is used for converting alphanumerical markings on the slide to digital slide ID. Optional attachment 1414 may be monitored by the computer 190 and ensures that replacing a slide is a documented event. The slide ID is usually printed, written or attached to the side of the slide and remains in view while the specimen is being inspected.

The actual location on the specimen is hidden from view while it is being observed by the objective which is in close proximity to the slide and much larger than the observed field of view.

Optionally, attachment 1414 further records an image of the entire slide 690, or large portion of it, the specimen 459 before the specimen is brought into focus. For example when the slide is well below the objective or as the slide is placed on the stage before the specimen is centered under the objective. Attachment 1414 may then identify the edges of the slide or markers on the slide and may infer what portion of the specimen is now observed in magnification. Optionally, the coordinates on the side, or the location on the specimen are recorded (for example as numerical coordinates or a mark on the image of the side or specimen) together with the microscopy image captured. Optionally, a motorized stage or graduated stage motion control allows identifying the location of the microscopically acquired image on the slide, and optionally allowing returning to the same spot for a second look.

Optionally the system 100 enables performing comparison of optical view of a specimen with a stored image in a side by side or overlay of the two images. Such presentation may be useful when thin sections of the same tissue are differently stained, thus different properties of the tissue are visually enhanced. It also may be useful to compare different slices of the same tissue taken at different depth within the extracted piece of tissue.

By creating a large database of images of normal and abnormal tissue of different type for example at the remote server 199, the user may view typical examples of similar tissue types and similar medical conditions, which were previously captured by himself of by other users, optionally at different locations and compare them to the specimen he is viewing. Optionally, digital zooming may be used if the stored image was taken at different magnification than the magnification used by the user. Optionally, the digital image is also re-oriented or shifted to match the optical image.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method for reviewing a specimen with an optical microscope comprising the steps of:

capturing through a beam splitter and a first polarizing filter a first digital image of a first portion of the specimen with a camera at a first time;

displaying the first digital image through an ocular of the microscope;

analyzing the first digital image to identify a first region of interest;

generating a first enhanced image corresponding to the first digital image, automatically adjusting color and brightness in the identified first region of interest, by a digital image projector, and projecting the first enhanced image through a second polarizing filter, which polarizes light perpendicular to the first polarizing filter, and by the beam splitter into the ocular of the microscope;

determining a first location of the first digital image with respect to a reference point;

capturing through the beam splitter and the first polarizing filter a second digital image of a second portion of the specimen with the camera at a second time after the first time;

analyzing the second digital image to identify a second region of interest;

generating a second enhanced image corresponding to the second digital image, automatically adjusting color and brightness in the identified second region of interest, by the digital image projector, and projecting the second enhanced image through the second polarizing filter and by the beam splitter into the ocular of the microscope;

determining a second location of the second digital image with respect to the reference point;

determining from the first digital image and the second digital image whether the specimen is at rest or in motion with respect to the reference point by evaluating average image blur or contrast gradients strength between the identified first region of interest and the identified second region of interest; and if the specimen has been in motion with respect to the reference point and is thereafter at rest for a specified time period, storing the second digital image, the second enhanced image, and the second location in a storage device.

2. The method of claim 1, wherein a portion of the digital image is darkened to provide greater contrast between the digital image and the enhanced image.

3. The method of claim 1, further comprising capturing an image encompassing the whole specimen and storing the image of the whole specimen with the digital image of the portion of the specimen.

4. The method of claim 3, wherein the image of the whole specimen further comprises calibration marks or labels near the specimen.

5. A system for reviewing a specimen with an optical microscope comprising:

the optical microscope having at least one objective lens and at least one ocular;

a beam splitter for diverting at least a portion of the light from the specimen to a digital camera and for diverting at least a portion of light from a digital image projector to the at least one ocular;

the digital camera for capturing, through the beam splitter and a first polarizing filter, a first digital image of a first portion of the specimen at a first time and then for capturing, also through the beam splitter and the first polarizing filter, a second digital image of a second portion of the specimen at a second time after the first time;

an image analysis module for analyzing the first digital image to identify a first region of interest and for analyzing the second digital image to identify a second region of interest;

the digital image projector for generating a first enhanced image corresponding to the first digital image, automatically adjusting color and brightness in the identified first region of interest, and projecting the first enhanced image into the at least one ocular by the beam splitter and through a second polarizing filter which polarizes light perpendicular to the first polarizing filter, and then for generating a second enhanced image corresponding to the second digital image, automatically adjusting color and brightness in the identified second region of interest, and projecting the second enhanced image into the at least one ocular also by the beam splitter and through the second polarizing filter; and a data processing unit for determining a first location of the first digital image with respect to a reference point, for determining a second location for the second digital image with respect to the reference point, and for determining from the first digital image and the second digital image whether the specimen is at rest or in motion with respect to the reference point by evaluating average image blur or contrast gradients strength between the identified first region of interest and the identified second region of interest; and wherein, if the specimen has been in motion with respect to the reference point and is thereafter at rest for a specified time period, the second captured digital image, the second enhanced image, and the second location are stored in a storage device.

6. The system of claim 5, wherein a portion of the digital image is darkened to provide greater contrast between the digital image and the enhanced image.

7. The system of claim 5, further comprising a second camera for capturing an image encompassing the whole specimen and storing the image of the whole specimen with the digital image of the portion of the specimen.

8. The system of claim 7 wherein the image of the whole specimen further comprises calibration marks or labels near the specimen.

9. The system of claim 5, further comprising a liquid crystal display in an optical train between the ocular and the objective lens for blocking at least a portion of the light arriving in the ocular from the objective to increase the visibility of the enhanced image from the digital image projector.

10. A computer program product for reviewing a specimen with an optical microscope comprising a processor, memory accessible from the processor for performing the steps of:

capturing through a beam splitter and a first polarizing filter a first digital image of a first portion of the specimen with a camera at a first time;

displaying the first digital image through an ocular of the microscope;

analyzing the first digital image to identify a first region of interest;

generating a first enhanced image corresponding to the first digital image, automatically adjusting color and brightness in the identified first region of interest, by a digital image projector, and projecting the first enhanced image through a second polarizing filter, which polarizes light perpendicular to the first polarizing filter, and by the beam splitter into the ocular of the microscope;

determining a first location of the first digital image with respect to a reference point;

capturing through the beam splitter and the first polarizing filter a second digital image of a second portion of the specimen with the camera at a second time after the first time;

analyzing the second digital image to identify a second region of interest;

generating a second enhanced image corresponding to the second digital image, automatically adjusting color and brightness in the identified second region of interest, by the digital image projector, and projecting the second enhanced image through the second polarizing filter and by the beam splitter into the ocular of the microscope;

determining a second location of the second digital image with respect to the reference point;

determining from the first digital image and the second digital image whether the specimen is at rest or in motion with respect to the reference point by evaluating average image blur or contrast gradients strength between the identified first region of interest and the identified second region of interest; and if the specimen has been in motion with respect to the reference point and is thereafter at rest for a specified time period, storing the second digital image, the second enhanced image, and the second location in a storage device.

11. The computer program product of claim 10, wherein a portion of the digital image is darkened to provide greater contrast between the digital image and the enhanced image.

12. The computer program product of claim 10, further comprising capturing an image encompassing the whole specimen and storing the image of the whole specimen with the digital image of a portion of the specimen.

13. The computer program product of claim 12, wherein the image of the whole specimen further comprises calibration marks or labels near the specimen.

* * * * *